(12) United States Patent
Davison et al.

(10) Patent No.: US 9,317,631 B2
(45) Date of Patent: Apr. 19, 2016

(54) SURGICAL GUIDE WITH CUT RESISTANT INSERTS

(71) Applicant: DePuy Synthes Products, Inc., Raynham, MA (US)

(72) Inventors: Andrew Charles Davison, West Chester, PA (US); Michael Barthold, West Chester, PA (US)

(73) Assignee: DePuy Synthes Products, Inc., Raynham, MA (US)

( * ) Notice: Subject to any disclaimer, the term of this patent is extended or adjusted under 35 U.S.C. 154(b) by 242 days.

(21) Appl. No.: 13/792,849

(22) Filed: Mar. 11, 2013

(65) Prior Publication Data

US 2014/0094811 A1    Apr. 3, 2014

Related U.S. Application Data

(60) Provisional application No. 61/642,063, filed on May 3, 2012, provisional application No. 61/645,890, filed on May 11, 2012, provisional application No. 61/699,938, filed on Sep. 12, 2012.

(51) Int. Cl.
| | |
|---|---|
| *A61B 17/17* | (2006.01) |
| *G06F 17/50* | (2006.01) |
| *A61B 17/15* | (2006.01) |
| *A61B 19/00* | (2006.01) |
| *A61F 2/46* | (2006.01) |

(52) U.S. Cl.
CPC ............ *G06F 17/5009* (2013.01); *A61B 17/15* (2013.01); *A61B 17/17* (2013.01); *A61B 17/1728* (2013.01); *A61B 17/1739* (2013.01); *A61B 19/50* (2013.01); *A61B 17/176* (2013.01); *A61F 2002/4649* (2013.01)

(58) Field of Classification Search
CPC ..... A61B 17/17; A61B 17/15; G06F 17/5009
USPC .............................................. 606/86 R, 87–89
See application file for complete search history.

(56) References Cited

U.S. PATENT DOCUMENTS

| | | |
|---|---|---|
| 5,042,983 A | 8/1991 | Rayhack |
| 5,098,383 A | 3/1992 | Hemmy et al. |
| 5,176,685 A | 1/1993 | Rayhack |
| 5,413,579 A * | 5/1995 | Tom Du Toit ................... 606/87 |
| 5,601,563 A | 2/1997 | Burke et al. |
| 5,860,981 A | 1/1999 | Bertin et al. |
| 5,876,204 A | 3/1999 | Day et al. |

(Continued)

FOREIGN PATENT DOCUMENTS

| | | |
|---|---|---|
| EP | 0468192 | 9/1996 |
| EP | 1216666 | 6/2002 |

(Continued)

OTHER PUBLICATIONS

U.S. Appl. No. 13/792,746, filed Mar. 11, 2013, Davison et al.

(Continued)

*Primary Examiner* — Christopher Beccia
(74) *Attorney, Agent, or Firm* — Baker & Hostetler LLP

(57) ABSTRACT

A resection guide can be configured to guide a resection tool toward a graft source, and can include a resection guide body made from a first material, and a guide member made from a second material. The second material is harder than the first material.

26 Claims, 24 Drawing Sheets

(56) References Cited

U.S. PATENT DOCUMENTS

| | | | |
|---|---|---|---|
| 5,916,220 A | 6/1999 | Masini | |
| 6,007,537 A * | 12/1999 | Burkinshaw et al. | 606/66 |
| 6,077,266 A | 6/2000 | Medoff | |
| 6,110,177 A | 8/2000 | Ebner et al. | |
| 6,978,188 B1 | 12/2005 | Christensen | |
| 7,621,919 B2 | 11/2009 | Williams, III et al. | |
| 7,758,345 B1 | 7/2010 | Christensen | |
| 8,086,336 B2 | 12/2011 | Christensen | |
| 8,177,822 B2 | 5/2012 | Medoff | |
| 8,439,926 B2 | 5/2013 | Bojarski et al. | |
| 8,725,465 B2 | 5/2014 | Hultgren et al. | |
| 8,775,133 B2 | 7/2014 | Schroeder | |
| 2002/0082604 A1* | 6/2002 | Abdelgany et al. | 606/79 |
| 2002/0138078 A1 | 9/2002 | Chappius | |
| 2004/0034361 A1* | 2/2004 | Dalton | 606/87 |
| 2004/0097946 A1 | 5/2004 | Dietzel et al. | |
| 2005/0043835 A1 | 2/2005 | Christensen | |
| 2005/0133955 A1 | 6/2005 | Christensen | |
| 2008/0195240 A1 | 8/2008 | Martin et al. | |
| 2008/0221569 A1 | 9/2008 | Moore et al. | |
| 2008/0275452 A1 | 11/2008 | Lang et al. | |
| 2009/0047165 A1* | 2/2009 | Syvanen et al. | 420/61 |
| 2009/0082774 A1* | 3/2009 | Oti et al. | 606/87 |
| 2009/0087276 A1 | 4/2009 | Rose | |
| 2009/0088758 A1 | 4/2009 | Bennett | |
| 2009/0092948 A1 | 4/2009 | Gantes | |
| 2010/0137873 A1 | 6/2010 | Grady, Jr. et al. | |
| 2010/0152782 A1 | 6/2010 | Stone et al. | |
| 2010/0168752 A1 | 7/2010 | Edwards | |
| 2010/0168753 A1 | 7/2010 | Edwards et al. | |
| 2010/0169057 A1 | 7/2010 | Hultgren et al. | |
| 2010/0216083 A1 | 8/2010 | Grobbee | |
| 2010/0262150 A1 | 10/2010 | Lian | |
| 2010/0292963 A1 | 11/2010 | Schroeder | |
| 2010/0324558 A1 | 12/2010 | Bickley et al. | |
| 2011/0008754 A1 | 1/2011 | Bassett et al. | |
| 2011/0092804 A1 | 4/2011 | Schoenefeld et al. | |
| 2011/0144698 A1 | 6/2011 | Buchbinder et al. | |
| 2012/0022604 A1 | 1/2012 | Polley et al. | |
| 2012/0029574 A1 | 2/2012 | Furrer et al. | |
| 2012/0109135 A1 | 5/2012 | Bailey | |
| 2012/0130686 A1 | 5/2012 | Graumann | |
| 2012/0141034 A1 | 6/2012 | Iannotti et al. | |
| 2012/0150243 A9 | 6/2012 | Crawford et al. | |
| 2012/0261848 A1 | 10/2012 | Haraszati | |
| 2012/0276509 A1 | 11/2012 | Iannotti et al. | |
| 2012/0289965 A1* | 11/2012 | Gelaude et al. | 606/87 |
| 2012/0303131 A1 | 11/2012 | Chana | |
| 2013/0072988 A1 | 3/2013 | Hulliger | |

FOREIGN PATENT DOCUMENTS

| | | |
|---|---|---|
| EP | 1854611 | 11/2007 |
| EP | 1808137 | 4/2010 |
| EP | 2208470 | 7/2010 |
| EP | 2062224 | 8/2010 |
| FR | 2847453 | 5/2004 |
| WO | WO 2004/039266 | 5/2004 |
| WO | WO 2005/032790 | 4/2005 |
| WO | WO 2011/070367 | 6/2011 |
| WO | WO 2011/071611 | 6/2011 |
| WO | WO 2011/080260 | 7/2011 |
| WO | WO 2011/103689 | 9/2011 |
| WO | WO 2012/027574 | 3/2012 |

OTHER PUBLICATIONS

U.S. Appl. No. 13/801,244, filed Mar. 13, 2013, Furrer et al.

Cevidanes et al., "Three-Dimensional Surgical Simulation", Am. J. Orthod. Dentofacial. Orthop., Sep. 2010, 138(3), 361-371.

Chapuis et al., "A New System for Computer-Aided Preoperative Planning and Intraoperative Navigation During Corrective Jaw Surgery", IEEE Trans. Inf. Technol. Biomed., May 2007, 11(3), 274-287.

DePuy Orthopaedics, Inc., "TruMatch Personalized Solutions", Oct. 27, 2011, 2 pages.

International Patent Application No. PCT/US2013/030131: International Search Report dated Jun. 25, 2013, 11 pages.

International Patent Application No. PCT/US2013/030139: Invitation to Pay Additional Fees dated Jun. 10, 2013, 5 pages.

Lubbers et al., "Surgical Navigation in Craniomaxillofacial Surgery: Expensive Toy or Useful Tool? A Classification of Different Indications", J. Oral Maxillofac. Surg., Jan. 2011, 69(1), 300-308.

Mavili et al., "Use of Three-Dimensional Medical Modeling Methods for Precise Planning of Orthognathic Surgery", J. Craniofac. Surg., Jul. 2007, 18(4), 740-747.

Olszewski et al., "Innovative Procedure for Computer-Assisted Genioplasty: Three-Dimensional Cephalometry, Rapid-Prototyping Model and Surgical Splint", Int. J. Oral Maxillofac. Surg., Jul. 2010, 39(7), 721-724.

International Patent Application No. PCT/US2013/030139: International Search Report dated Aug. 6, 2013, 19 pages.

International Patent Application No. PCT/US2013/059226; International Search Report dated Dec. 2, 2013, 10 pages.

Klein et al., A Computerized Tomography (CT) Scan Appliance for Optimal Presurgical and Preprosthetic Planning of the Implant Patient, Practical Periodontics & Aesthetic Dentistry, vol. 5, No. 6, 1993, 33-39.

U.S. Appl. No. 13/900,817, filed May 23, 2013, Davison et al.

* cited by examiner

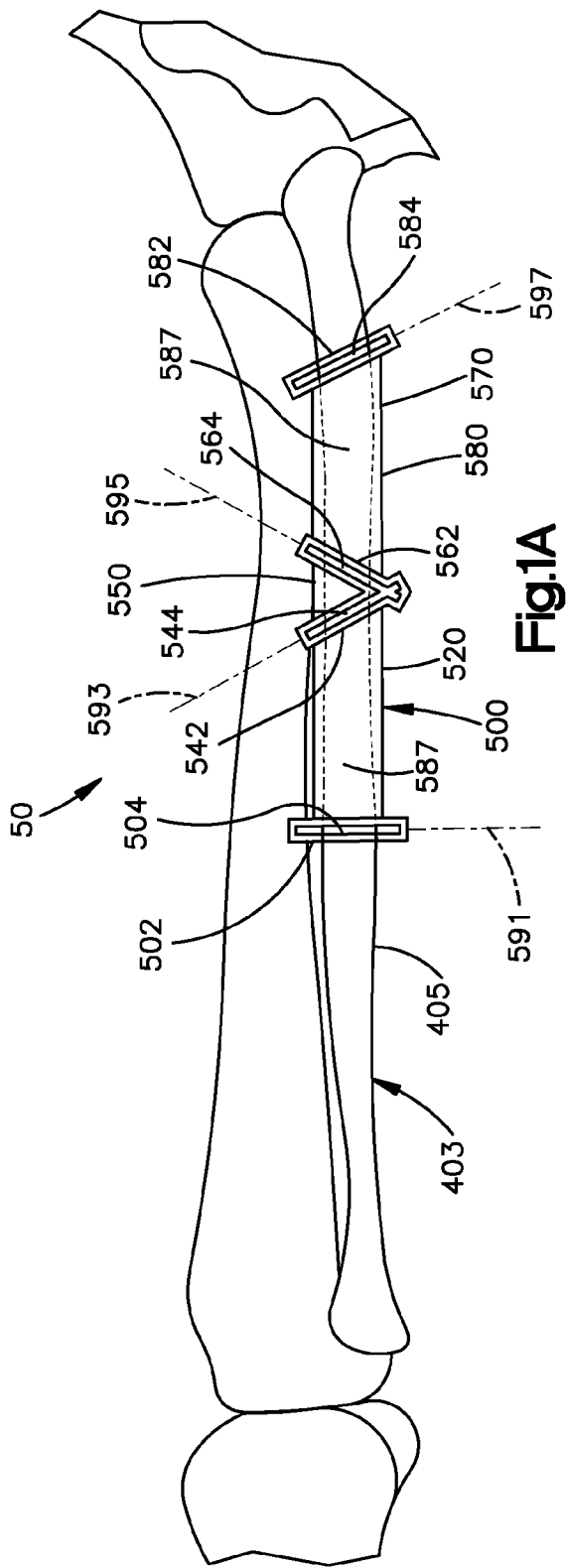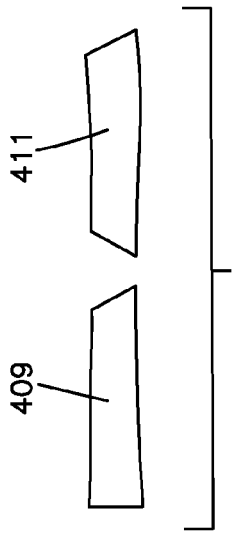
Fig.1A
Fig.1B

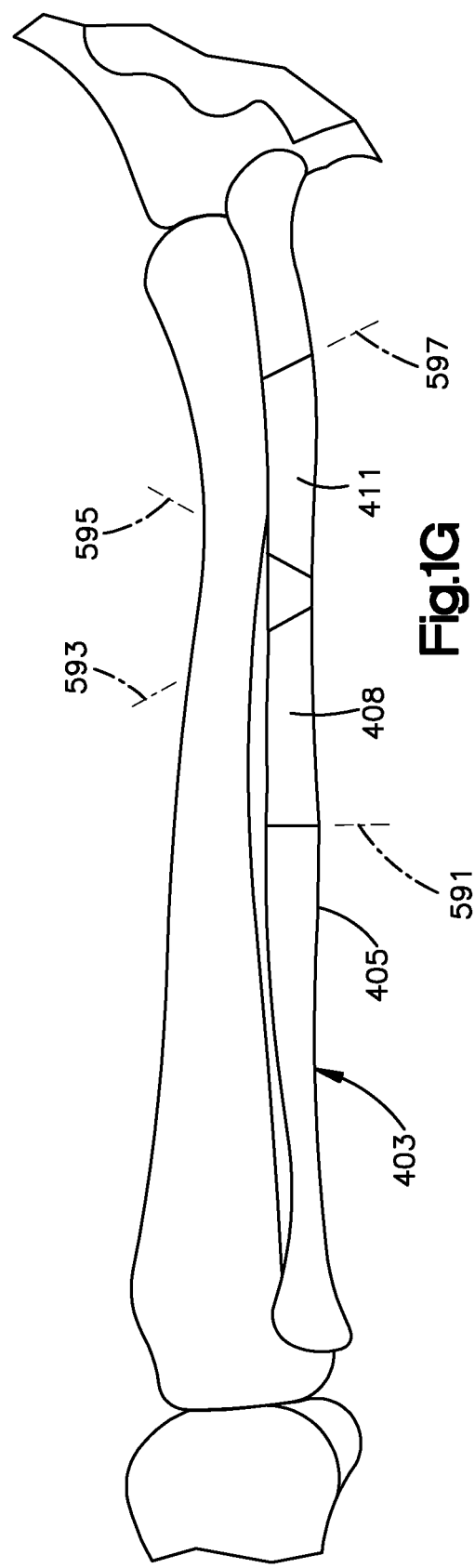

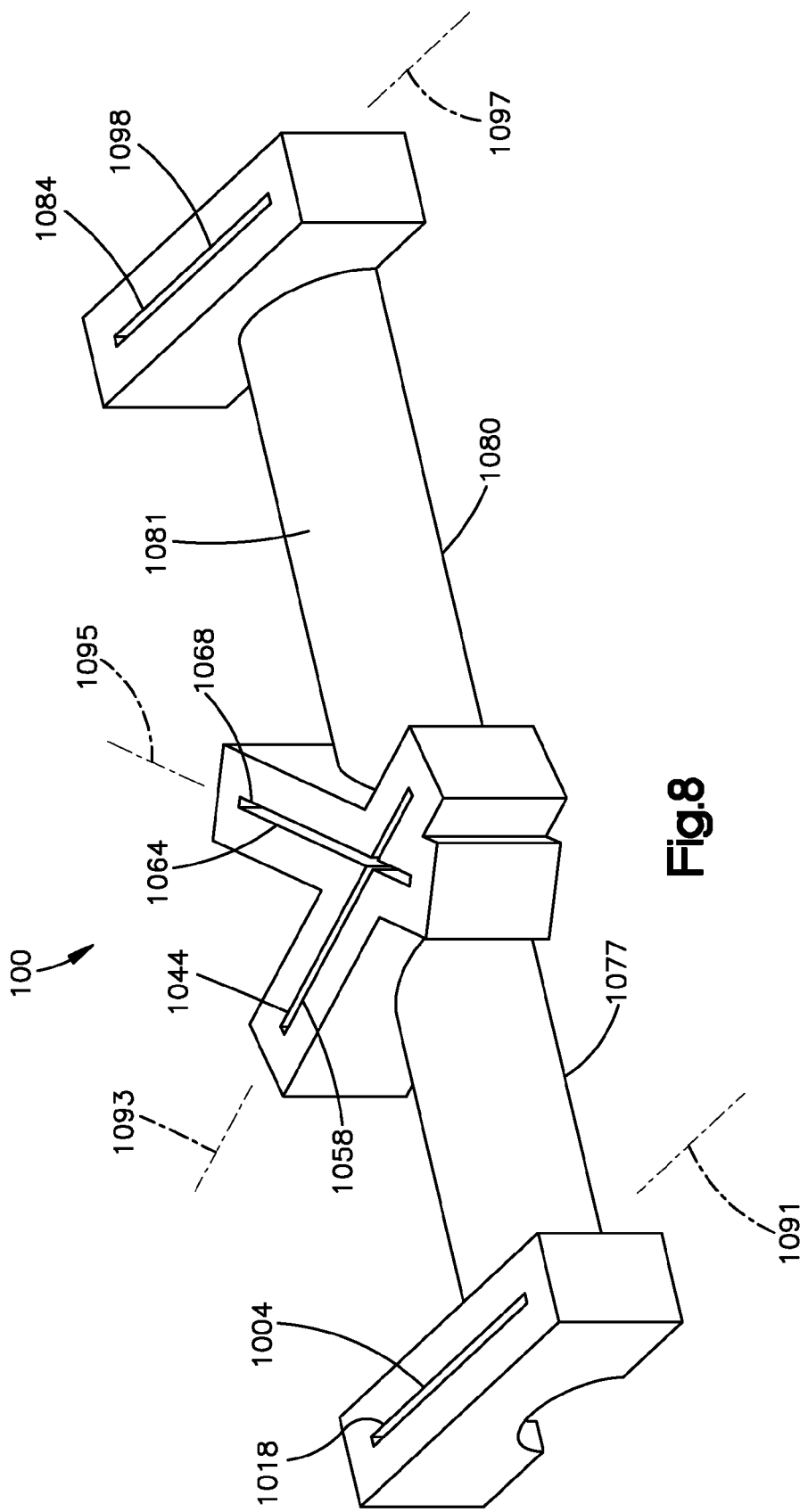

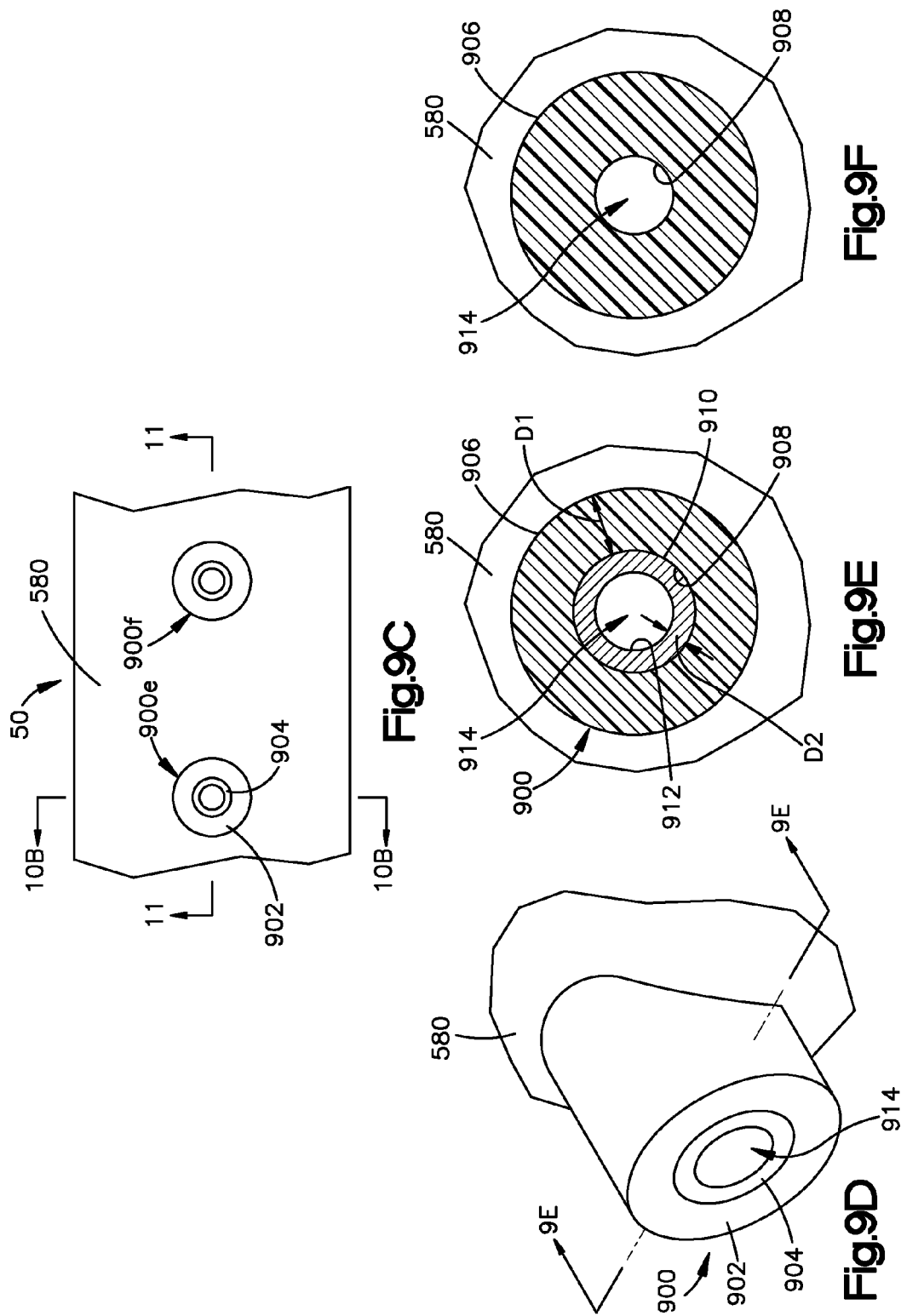

SURGICAL GUIDE WITH CUT RESISTANT INSERTS

CROSS-REFERENCE TO RELATED APPLICATIONS

This application claims the benefit of U.S. Provisional Patent Application Ser. No. 61/642,063 filed May 3, 2012, U.S. Provisional Patent Application Ser. No. 61/645,890 filed May 11, 2012, and also U.S. Provisional Patent Application Ser. No. 61/699,938 filed Sep. 12, 2012, the entire disclosures of which are incorporated by reference into this patent application for all purposes.

FIELD OF DISCLOSURE

The present application generally relates to a surgical resection guide, and in particular relates to a surgical resection guide that is configured to guide one or more tools to cut and/or prepare a tissue, such as bone.

BACKGROUND

Many surgical procedures require accurate cuts of bone. For example, in mandibular reconstruction surgery, deficient or infectious portions of the mandible may be removed from the patient and replaced with bone graft. In some instances, a surgeon performing orthognathic surgery typically makes several cuts on the mandible to properly fit a bone graft. To make an accurate cut, the surgeon may use a patient specific resection guide to guide the motion of the resection tool toward the bone. The resection guide can also be used while cutting a bone portion from other parts of the patient to harvest bone grafts.

The resection guide may wear over time due to the friction exerted by the resection tool on the resection guide during use. This wear may reduce the accuracy of the resection guide and produce wear debris. Wear debris stemming from the resection guide could be detrimental to the long-term efficacy of the bone graft.

SUMMARY

The present disclosure relates to surgical system for reconstructing at least a portion of a tissue body with a graft. The surgical system can include a resection guide that is configured to guide a one or more tools toward a graft source. In one embodiment, the resection guide can generally include a resection guide body and a guide member. The resection guide body can be at least partially made from a first material, and defines an upper body surface and a lower body surface that is opposite the upper body surface and positioned to be placed against the graft source. Further, the resection guide body can define a first resection guide opening and a second resection guide opening that is spaced from the first resection guide opening. The first and second resection guide openings can extend through upper and lower body surfaces. The guide member can be configured to be at least partially inserted in at least one of the first resection guide opening or the second resection guide opening. In particular, the guide member can include a guide member body. The guide member can define a guide member opening that extends through the guide member body and is elongate along a graft resection axis. The guide member opening can be configured to receive at least a portion of the resection tool such that the guide member guides a movement of the resection tool along the graft resection axis when the resection tool is received in the guide member opening. The guide member can be at least partially made of a second material that is harder than the first material.

In an embodiment, the first material of the resection guide body has a first hardness, and the second material of the guide member has a second hardness. The second hardness can be greater than the first hardness. Specifically, the first material can have a Brinell hardness ranging between about 1 HBS 10/100 and about 3 HBS 10/100. In one embodiment, the second material can have a Brinell hardness ranging between about 10 and about 200 HB. The second material can be a metallic material, such as stainless steel or aluminum. The first material can be a polymeric material.

In an embodiment, at least a portion of the guide member can be removably disposed in the first resection guide opening or the second resection guide opening. The guide member can include at least one tab that protrudes from the guide member body, and the tab is configured to abut at least a portion of the upper body surface when the guide member body is fully seated into the first resection guide opening or the second resection guide opening. The tab can be cantilevered from the guide member body. The guide member can include a first tab and a second tab that is cantilevered from the guide member body. The second tab can be configured to abut at least a portion of the upper body surface when the guide member body is fully seated in the first resection guide opening or the second resection guide opening. The guide member body can define a front wall, a rear wall opposite to the front wall, and a pair of side walls that extend between the front and rear walls. The front wall, the rear wall, and the side walls can define the guide member opening. The first tab can protrude from the front wall, and the second tab protrudes from the rear wall. The side walls can be elongate along the graft resection axis.

In an embodiment, the resection guide can further define a third resection guide opening and a fourth resection guide opening that is spaced from the third resection guide opening. The third and fourth resection guide openings can be configured to receive at least a portion of the resection tool so as to resect a second graft portion from the graft source. The guide member can be configured to be selectively inserted into each of the first, second, third, and fourth resection guide openings so as to guide the resection tool along the graft resection axis. The resection guide body can include first and second inner surfaces that at least partially define the first and second resection guide openings, respectively. The guide member can be segmented so as to define a plurality of discrete guiding components configured to be mounted to at least one of the first or second inner surfaces. The discrete guiding components can be made from the second material. The discrete guiding components and the respective first or second inner surface can define complementary engagement members that are configured to mate so as to attach the discrete guiding components to the respective inner surface. The engagement member of each of the guiding components can include a tongue, and the engagement member of the respective inner surface can define a groove configured to receive the tongue. The tongue can be tapered so as to so as to be press-fit within the respective groove. The guide member can be a first guide member configured to be attached to the first inner surface. The resection guide can further include a second guide member that is segmented so as to define a plurality of discrete guiding components that configured to be attached to the second inner surface. The second material can be at least partially made from a laser-sintered metallic material. The second material can be made using a direct metal laser sintering process. The first material can be stereolithographic.

In an embodiment, the resection guide can include a metallic resection guide body that defines an upper body surface and a lower body surface opposite the upper body surface and configured to face the graft source. The resection guide body can define a first and second resection guide openings that are spaced from each other and extend from the lower body surface through the upper body surface. The first and second resection guide openings can define respective first and second graft resection axes that are configured to receive a portion of the resection tool and guide the resection tool along the respective first and second resection guide openings so as to resect a graft portion from the graft source. The resection guide body can define first and second inner surfaces that at least partially define the first and second resection guide openings and are configured to contact the resection tool as the resection tool is guided along the respective first and second graft resection axes. The first and second resection guide openings are devoid of inserts that are discrete with the resection guide body. The metallic resection guide body is laser-sintered. The first and second axes are angularly offset with respect to each other. The resection guide body can be made from a metallic material that has a Brinell hardness ranging between about 10 HB and about 200 HB. For example, the resection guide body can be made from a metallic material that has a Brinell hardness of about 120 HB.

BRIEF DESCRIPTION OF THE DRAWINGS

The foregoing summary, as well as the following detailed description of a preferred embodiment, are better understood when read in conjunction with the appended diagrammatic drawings. For the purpose of illustrating the invention, the drawings show an embodiment that is presently preferred. The invention is not limited, however, to the specific instrumentalities disclosed in the drawings. In the drawings:

FIG. 1A is a perspective view of a surgical resection guide placed over a graft source according to an embodiment of the present disclosure;

FIG. 1B is a front elevation view of first and second graft portions harvested from the graft source shown in FIG. 1A;

FIG. 1G is a perspective view of a virtual model of a graft source, showing surgically planned resection suitable to create the first and second graft portions illustrated in FIG. 1B;

FIG. 8 is a perspective view of a resection guide in accordance with an embodiment of the present disclosure that is made of a single material.

FIG. 9C is a plan view of a portion of the resection guide of FIG. 9A, illustrating a drilling guide member;

FIG. 9D is a perspective view of drilling guide member shown in FIG. 9C;

FIG. 9E is a cross-sectional view of the drilling guide member taken along line 9E-9E in FIG. 9C;

FIG. 9F is a cross-sectional view of the drilling guide member taken along line 9E-9E in FIG. 9C, according to another embodiment of the present disclosure;

DETAILED DESCRIPTION OF THE DRAWINGS

Figure 1C:
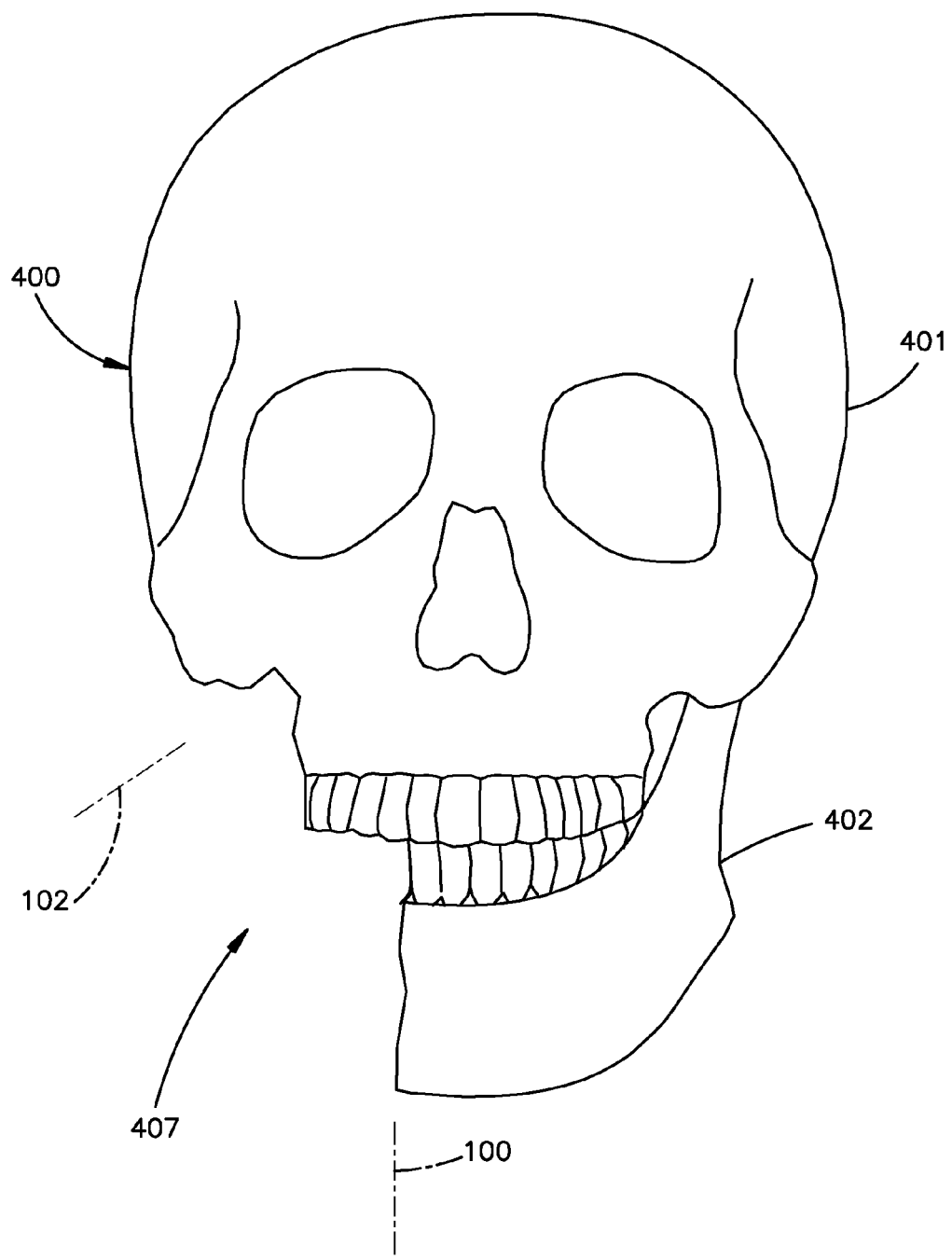
FIG. 1C is a perspective view of the skull of FIG. 1A, showing a mandible that has been resected so as to define a cavity.

Certain terminology is used in the following description for convenience only and is not limiting. The words "right", "left", "lower" and "upper" designate directions in the drawings to which reference is made. The words "proximally" and "distally" refer to directions toward and away from, respectively, the surgeon using the surgical device. The words, "anterior", "posterior", "superior", "inferior" and related words and/or phrases designate preferred positions and orientations in the human body to which reference is made and are not meant to be limiting. The terminology includes the above-listed words, derivatives thereof and words of similar import.

Figure 1D:
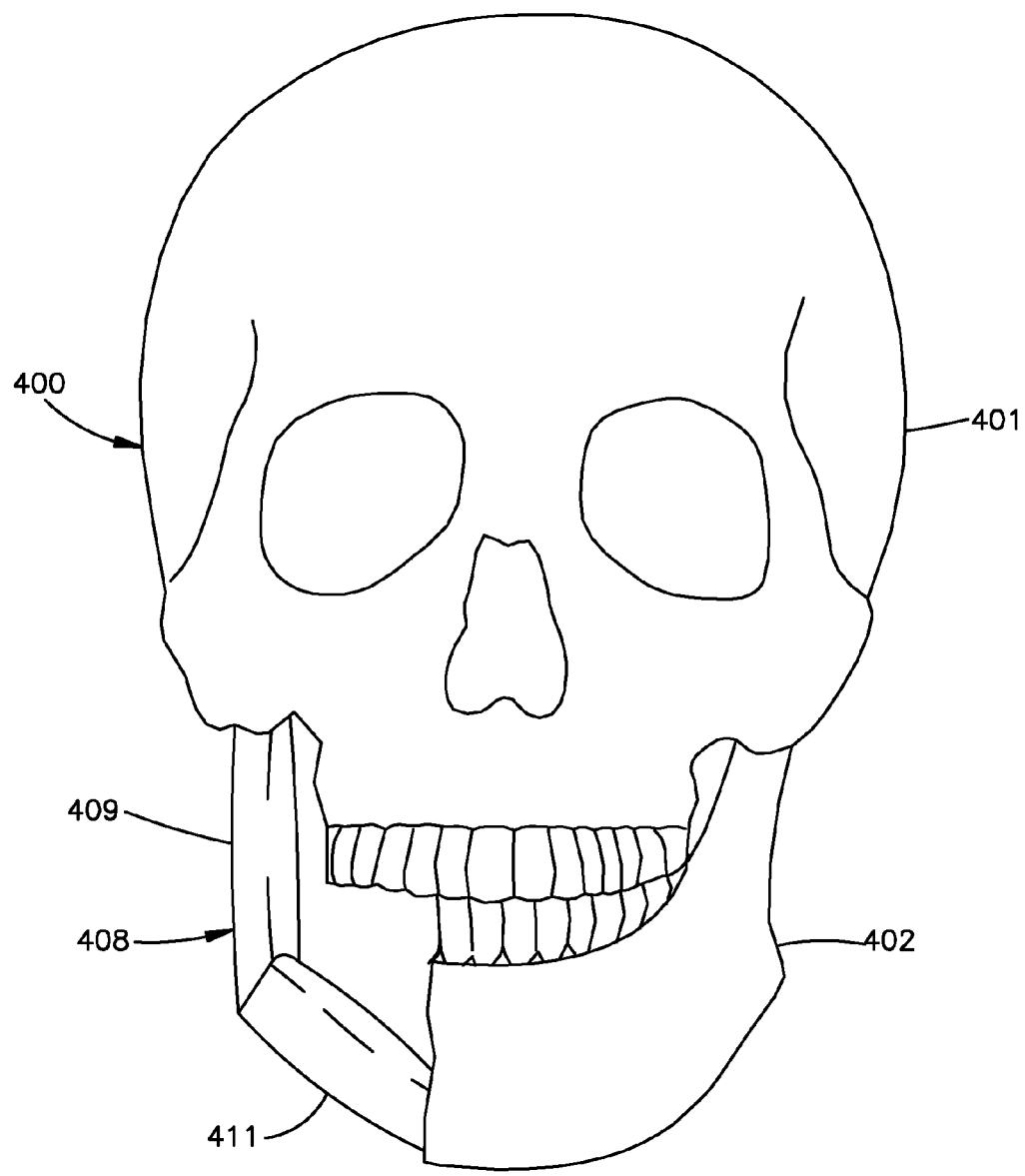
FIG. 1D is a perspective view of a reconstructed mandible, showing a graft formed by coupling the first graft portion and the second graft portion shown in FIG. 1B inserted into the cavity shown in FIG. 1C.

With reference to FIG. 1A, a surgical system 10 be used to reconstruct at least a portion of a tissue body 400 with a graft 408 (FIG. 1D). The tissue body 400 can include at least one of anatomical tissue or a tissue substitute. The term anatomical tissue can include hard tissue such as bone. For instance, the tissue body 400 can include a mandible 402. The surgical system 10 can be configured to remove a diseased tissue portion 404 (FIG. 1E), such as a damaged tissue portion, from the tissue body 400, harvest the graft 408 from a graft source 403, and replace the diseased tissue portion 404 with the graft 408.

In an embodiment, the surgical system 10 can include a resection guide 50 that is configured to harvest the graft 408 (FIG. 1E) from the graft source 403 and prepare the graft 408 for positioning and securement to the tissue body 400. In particular, the resection guide 50 can be configured to guide a resection tool 300 (FIG. 1E) toward the graft source 403 along one or more predetermined graft resection axes. For instance, the resection guide 50 can be configured to a guide the resection tool 300 along graft resection axes 591, 593, 595, and 597. The graft resection axes 591, 593, 595, and 597 can be predetermined with the aid of virtual models of the graft source 403 and diseased tissue portion 404 (FIG. 1E) as discussed detail below. In other embodiments, the resection guide can also be configured to guide a drilling tool 310 (FIGS. 9A and 12A) into the tissue body 400 or graft source 403. For instance, the resection guide can be configured to guide a tool, such as drill bit along an anchor location axis 319 to form a bore in the graft source 403 or tissue body 400 that is sized to receive an anchor therein, for instance for coupling a bone plate to the graft 408 and tissue body 400. The location and orientation of the anchor location axis 319 can also be predetermined with the aid of virtual models of the graft source 403, the tissue body 400, including the diseased tissue portion 404 (FIG. 1E), and a bone fixation element, as discussed detail below. Thus, the resection guide 300 can be patient specific. That is, the resection guide 50 can guide the resection tool 300 toward the graft source 403 to create one or more graft portions that are sized and shaped to properly replace the diseased tissue portion 404 (FIG. 1E) of the tissue body 400.

Figure 9A:
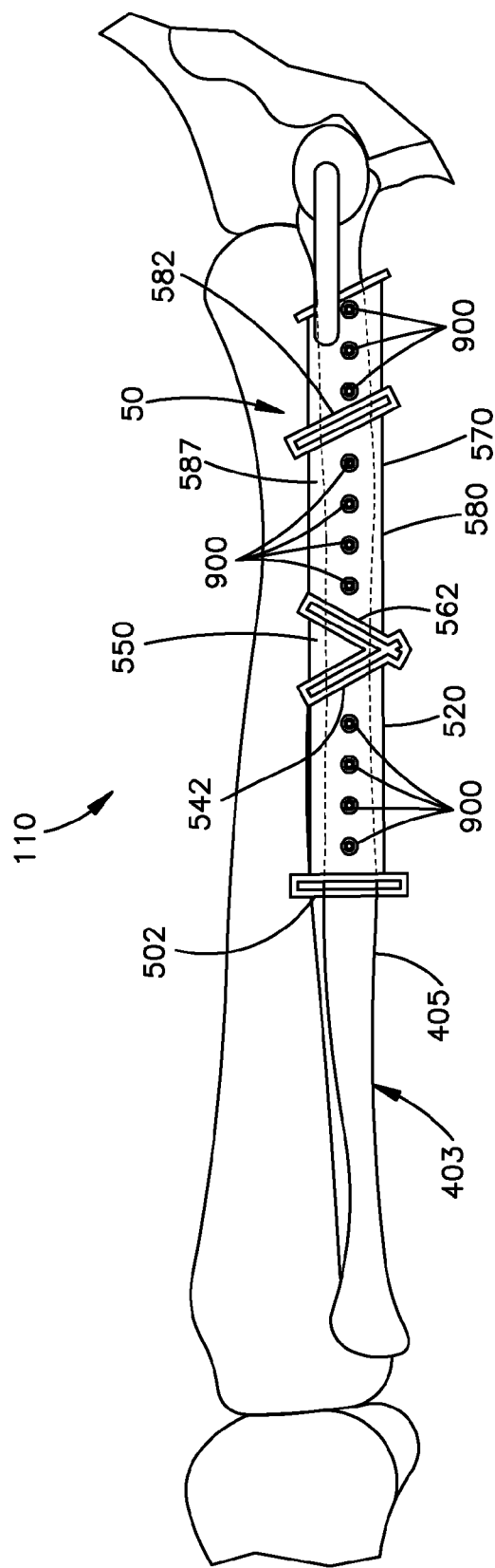
FIG. 9A is a perspective view of a resection guide placed over a graft source, including a resection guide body and guide members, according to another embodiment of the present disclosure.

With reference to FIG. 1A, the resection guide 50 can be configured to guide a resection tool 300 (FIG. 1E) toward the graft source 403 to resect a portion of the graft source 403 in order to create the graft 408 (FIG. 1D). The graft 408 can be shaped and sized to replace the diseased tissue portion 404 (FIG. 1E) that is removed from the tissue body 400. The graft source 403 can be a long bone, such as the fibula 405. Alternatively, the graft source 403 can be other bones such as the scapula, hip, forearm, among others. The resection guide 50 can include a resection guide body 580 that in turn can include one or more resection guide supporting members. As further detailed below, the resection guide can include one or more drill guide member 900 (FIG. 9A).

Each resection guide supporting member is configured to support a guide member as discussed in detail below. In the depicted embodiment, the resection guide body 580 can include a first resection guide supporting member 502, a second resection guide supporting member 542, a third resection guide supporting member 562, and a fourth resection guide supporting member 582.

The first resection guide supporting member 502 can define a first resection guide opening 504. Thus, the resection guide body 580 can define the first resection guide opening 504. The first resection guide opening 504 can be shaped and oriented relative to the resection guide body 580 such that the resection guide opening 504 can guide the resection tool 300 (FIG. 1E) along a first resection axis 591 defined along the graft source 403 when the resection guide 50 is coupled to the graft source 403.

The second resection guide supporting member 542 can define a second resection guide opening 544. Thus, the resection guide body 580 can define the second resection guide opening 544. The second resection guide opening 544 can be spaced from the first resection guide opening 504. The first resection guide opening 504 and the first resection guide opening 544 can extend through the upper body surface 581 and the lower body surface 577. The second resection guide opening 544 can be shaped and oriented relative to the resection guide body 580 such that the second resection guide opening 544 can guide the resection tool 300 (FIG. 1E) along a second graft resection axis 593 defined along the graft source 403 when the resection guide 50 is coupled to the graft source 403.

The third resection guide supporting member 562 can define a third resection guide opening 564. The third resection guide opening 564 can be shaped and oriented relative to the resection guide body 580 such that the third resection guide opening 564 can guide the resection tool 300 (FIG. 1E) along a third graft resection axis 595 when the resection guide 50 is coupled to the graft source 403.

The fourth resection guide supporting member 582 can define a fourth resection guide opening 584. The fourth resection guide opening 584 can be shaped and oriented relative to the resection guide body 580 such that the fourth resection guide opening 584 can guide the resection tool 300 (FIG. 1E) along a fourth resection graft axis 597 when the resection guide 300 is coupled to the graft source 403. The resection guide 50 can further defines the third resection guide opening 564 and the fourth resection guide opening 584 that is spaced from the third resection guide opening 564. The third and fourth resection guide openings 564 and 584 can be configured to receive at least a portion of the resection tool 300 so as to resect a second graft portion 411 from the graft source 403. The resection guide body 580 can define more than four resection guide openings. Also, the resection guide body 580 can define fewer than four resection guide openings.

With continuing reference to FIG. 1A, the resection guide body 580 can further include a first connection member 520 that couples the first resection guide supporting member 502 to the second resection guide supporting member 542, a second connecting member 550 that couples the second resection guide supporting member 542 to the third resection guide supporting member 562, and a third connecting member 570 that couples the third resection guide supporting member 562 to the fourth resection guide supporting member 584. The resection guide body 580 can further define one or more holes 587 that are configured to receive a fastener, such as a bone screw. The fasteners can be inserted through the holes 587 to fix the resection guide body 580 to the graft source 403. The holes 587 can be located, for example, along the first connecting member 520 and the third connecting member 580.

With continuing reference to FIG. 1A, the resection guide 50 can be shaped and contoured to fit only over a portion of the graft source 403 such that the resection guide openings 504, 544, 564, and 584 are substantially aligned with the graft resection axes 591, 593, 595, and 597, respectively. Thus, in operation, the resection guide 50 can be placed on the graft source 403 such that the resection guide openings 504, 544, 564, and 584 are substantially aligned with the graft resection axes 591, 593, 595, and 597, respectively. Then, the resection guide 50 can be coupled to the graft source 403 by, for example, inserting fasteners through the holes 587 and into the graft source 403. The resection tool 300 (FIG. 1E) can be inserted through the first resection guide opening 504 to make a resection, such as a cut, into the graft source 403 along the first graft resection axis 591. The resection tool 300 (FIG. 1C) can be inserted through the second resection guide opening 544 and into the graft source 403 to make a resection, such as a cut, into the graft source 403 along the second graft resection axis 593. Resections can be made to the graft source 403 along the first graft resection axis 591 and the second graft resection axis 593 to obtain the first graft portion 409 (FIG. 1B). The resection tool 300 (FIG. 1A) can be inserted through the third resection guide opening 564 and into the graft source 403 to make a resection, such as a cut, into the graft source 403 along the third graft resection axis 595. Further, the resection tool 300 (FIG. 1A) can be inserted through the fourth resection guide opening 584 and into the graft source 403 to make a resection, such as a cut, into the graft source 403 along the fourth resection axis 597. Resections can be made to the graft source 403 along the third graft resection axis 595 and the fourth graft resection axis 597 to obtain a second graft portion 411 (FIG. 1B). The resection guide 50 can then be detached from the graft source 403.

Figure 1E:
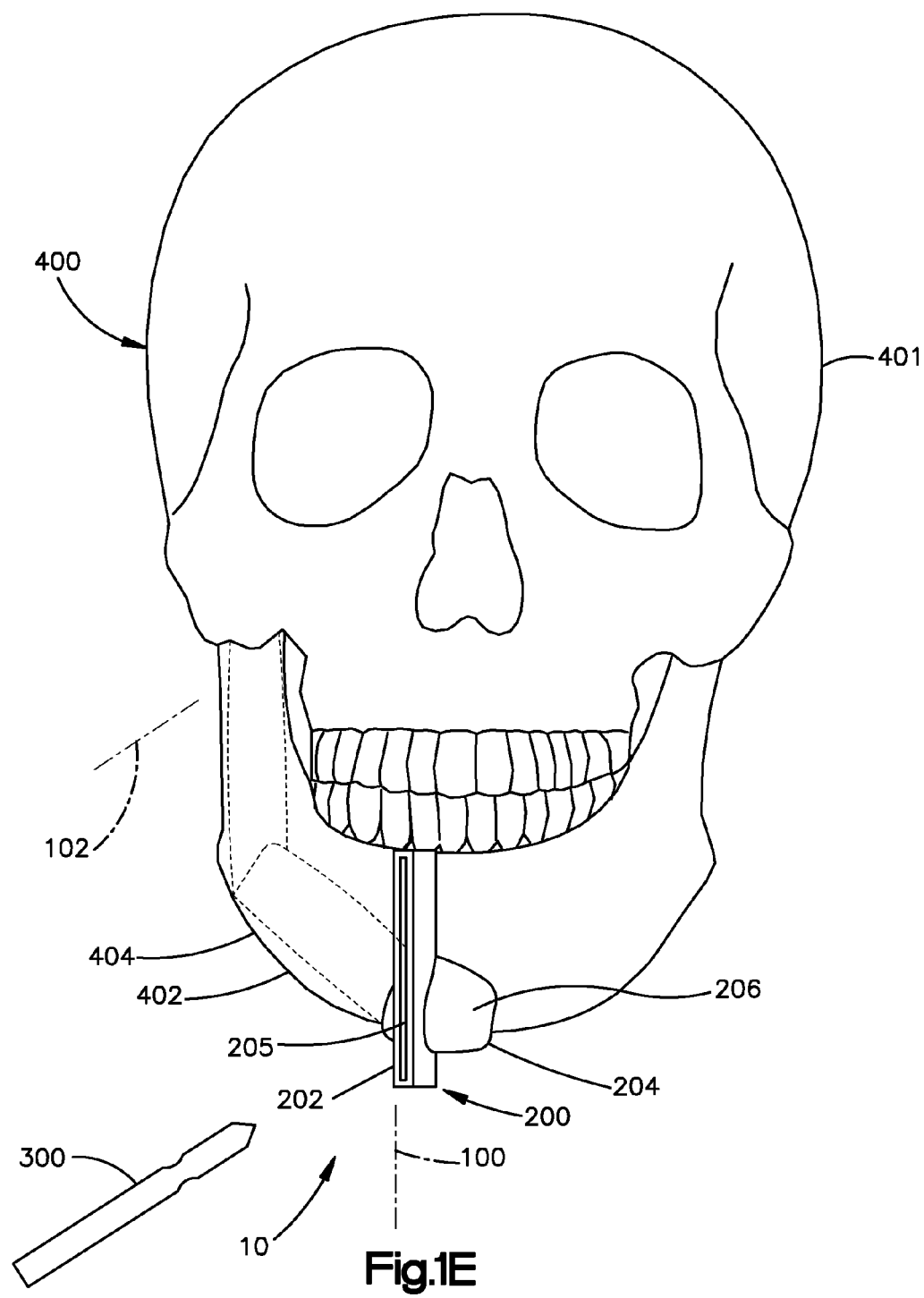
FIG. 1E is perspective view of a skull that includes a mandible, which in turn includes a diseased tissue portion, and a surgical resection guide coupled to the mandible.

With reference to FIG. 1B, after making resection into the graft source 403 along the graft resection axes 591, 593, 595, and 597, the first graft portion 409 and the second graft portion 411 can be removed from the graft source 403 (FIG. 1E). At this point, the first graft portion 409 and the second graft portion 411 can be two separate elements. However, the first graft portion 409 and the second graft portion 411 can be coupled to each other to form the graft 408 (FIG. 1D). In other words, the first graft portion 409 and the second graft portion 411 can cooperate to define the graft 408.

With reference to FIG. 1C, a tissue portion of the tissue body 400, such as the diseased tissue portion 404 (FIG. 1E), can be resected from the tissue body 400, thereby forming a cavity 407. In the depicted embodiment, the cavity 407 is defined by the resected or cut portion of the ramus at one end, and resected or cur portion the mental protuberance at the other end of the cavit. The first graft portion 409 and the second graft portion 411 can be interconnected to form the graft 408, which is shaped and sized to fit in the cavity 407 so as to replace the tissue portion removed from the tissue body 400.

With reference to FIG. 1D, the first graft portion 409 and the second graft portion 411 can cooperate to define the graft 408. For example, the first graft portion 409 and the second graft portion 411 can be coupled to the tissue body 400 and to each other, such that the first graft portion 409 and the second graft portion 411 can together fit in the cavity 407, thereby replacing the tissue portion previously removed from the tissue body 400. As discussed above, the first graft portion 409 and the second graft portion 411 can be coupled to each other so as to define the graft 408. Thus, the graft 408 can replace the tissue portion removed from the tissue body 400, such as the diseased tissue portion 404 (FIG. 1A).

With reference to FIG. 1E, the surgical system 10 can further include the resection tool 300 that is configured to resect, such as cut, the tissue body 400, and a resection guide 200, that is configured to be coupled to the tissue body 400 to guide the movement of the resection tool 300 toward the tissue body 400. The surgical system 10 can also include drilling tool 310 configured to form anchor locations in the tissue body 400 or graft source 403 as detailed below. The resection guides can also be configured to guide movement of the drilling tool 310 toward the tissue body 400 (FIG. 12A) or graft source 403 (FIG. 9A).

The resection tool 300 is configured to resect, such as cut, the tissue body 400, and can be a chisel, a saw, a blade, or any tool capable of resecting, such as cutting, the tissue body 400. The resection guide 200 can be configured to guide advancement of the resection tool 300 toward the tissue body 400 and can include a resection guide body 202 and a connecting member 204 connected to the resection guide body 202. The resection guide body 202 can define a resection guide opening 205 that is configured and sized to receive at least a portion of the resection tool 300. The resection guide opening 205 can also be configured and sized to receive a guide member as described below. The connecting member 204 can be configured to be coupled to the tissue body 400 at the desired resection site. For example, the connecting member 204 can be configured to be coupled to the tissue body 400 at a first resection site defined along the first resection axis 100. Thus, the connecting member 204 can be contoured to mirror the shape of a portion of the tissue body 400 along the first resection axis 100 so that the connecting member 204 substantially fits only over the portion of the tissue body 400 located along the first resection axis 100. Since the tissue body 400 of different patients have different shapes and sizes, the connecting member 204 can be created to fit over the desired resection site of a specific patient. That is, the connecting member 204, and thus the resection guide 200, can be patient specific.

To create a patient specific resection guide 200, a virtual three-dimensional model of a patient's tissue body 400, such as a skull 401, can be created using any suitable technology, such as x-ray computed tomography (CT) or any technology capable of mapping the tissue portion 400. For example, a virtual three-dimensional model of the patient's skull 401 can be created using a suitable CT machine. The skull 401 includes the mandible 402. Thus, a virtual model of the mandible 402 can also be created using the CT machine. Then, a clinician, such as a physician, assess the virtual model of the tissue body 400 to determine what portion of the tissue body 400 should be removed and replaced with a graft. The clinician can then determine the appropriate resection sites. For example, in the depicted tissue body 400, the clinician has determined that the tissue body 400 should be resected along the resection axes 100 and 102 in order to remove a diseased tissue portion 404 of the mandible 402. As used herein, the diseased tissue portion 404 can include damaged tissue portion. However, it is envisioned that the other portions of the tissue body 400 can be removed, and thus, the resection axes can be located at other positions as desired. After determining the appropriate resection sites as defined by the resection axes 100 and 102, the resection guide 200 can be created to fit over a specific resection site (as defined by, for example, the first resection axis 100) of the patient. That is, the connection member 204 can be shaped and sized to fit only over the resection site identified in the virtual model of the patient's tissue body 400.

Figure 1F:
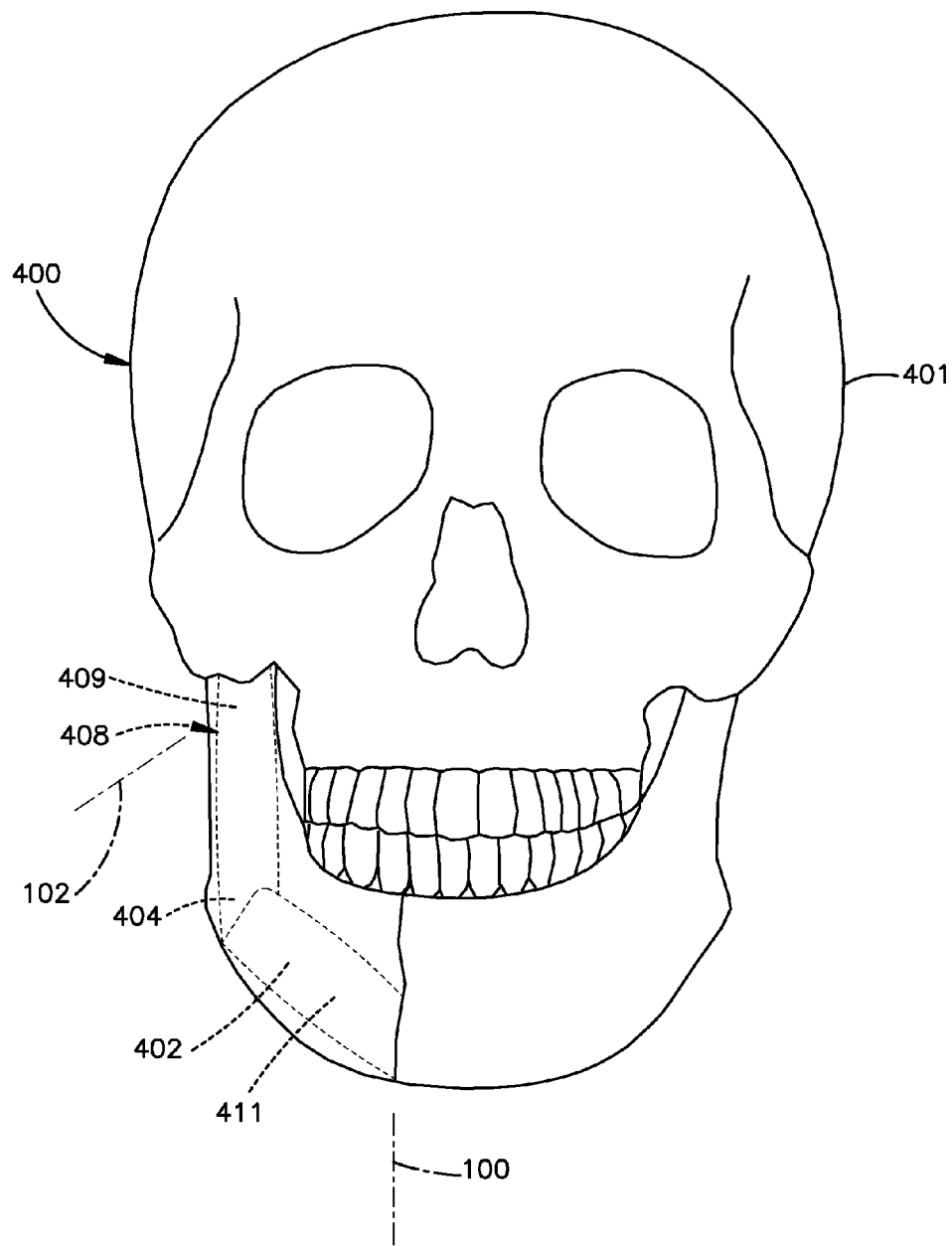
FIG. 1F is a perspective view of a virtual model of the skull shown in FIG. 1E, showing a graft superimposed over the diseased tissue portion.

With continuing reference to FIG. 1F, after determining the resection sites (as defined by resection axes 100 and 102), the appropriate graft size and shape can be determined. For example, a virtual model of an appropriate graft 408 can be superimposed over tissue body portion to be replaced, such as the diseased tissue portion 404, to determine the virtual model of the graft 408 has the proper size and shape. In the depicted embodiment, the virtual model of the graft 408 can include two portions, namely: a first graft portion 409 and a second graft portion 411. The first graft portion 409 and the second graft portion 411 can cooperate to define the graft 408. However, it is envisioned that the graft 408 can be a monolithic structure or can include more two portions. The graft 408 can be virtually designed so that it can be acquired from the same patient. That is, the graft 408 can be an autologous graft. Preferably, the first and second graft portions 409 and 411 can be designed such that the bone graft 408 can be harvested from a vascularized bone graft source, such as the fibula. Vascularized bone graft is preferred because these grafts provide better blood supply than non-vascularized bone grafts and thereby can lead to faster healing. However, it is contemplated that the graft 408 can be harvested from a non-vascularized bone graft source.

As seen in FIG. 1G, the first graft portion 409 and the second graft portion 411 can be oriented at an oblique angle relative to each other when these portions are virtually superimposed over the diseased portion 404. However, in their natural state, the first graft portion 409 and the second graft portion 411 can stem from the same graft source, and can therefore be aligned with each other. For example, the virtual models of the first graft portion 409 and the second graft portion 411 can be virtually removed from the virtual model of the patient's mandible 402, unfolded, and then aligned with a virtual model of a graft source 403, such as a fibula 405, to determine the appropriate location of the resection sites in the graft source 403. In the depicted embodiment, it can be appreciated that resections should be made in the graft source 403, such as the fibula, along a first graft resection axis 591, a second graft resection axis 593, a third graft resection axis 595, and a fourth graft resection axis 597 to obtain a graft that has the proper size and shape to replace the resected portion, such as the diseased tissue portion 404, of the tissue body 400. In particular, according to the virtual model of that particular patient, the graft source 403 can be resected along the graft resection axes 591 and 593 to harvest the first graft portion 408. Similarly, the graft source 403 can be resected along resection axes 595 and 597 to harvest the second graft portion 411. The location and orientation of the graft resection axes 591, 593, 595, and 597 in the virtual model of the graft source 403 can serve as guidelines to create a resection guide 50 (FIG. 1A) capable of facilitating resection along those same resection axes in the physical graft source 403. The resection guide 50 (FIG. 1A) can be shaped and contoured to fit only over a portion of the graft source 403 such that its resection guide opening (as discussed below) are aligned with the graft resection axes 591, 593, 595, and 597.

Referring again to FIG. 1E, once the resections have been virtually planned as discussed above, the resection guide 200 can be placed over the tissue body 400 such that the resection guide opening 205 is substantially aligned with the first resection axis 100. As discussed above, the connection member 204 can be shaped and contoured to fit only over the desired resection site such that the resection guide opening 205 is substantially aligned with the resection axis 100. The connection member 204 can be coupled to the tissue body 400 at the desired resection site. For instance, the connecting member 204 can define one or more holes 206 configured to receive a fastener, such as a bone screw. One or more fasteners can be inserted through the holes 206 to couple the resection guide 200 to the tissue body 400. The resection tool 300 can then be inserted through the resection guide opening 205, and advanced toward the tissue body 400 to resect the tissue body 400 along the first resection axis 100.

With reference to FIG. 1G, the graft 408 can replace the tissue portion removed from the tissue body 400, such as the diseased tissue portion 404 (FIG. 1E). In the depicted embodiment, the first graft portion 409 and the second graft portion 411 can be positioned in the tissue body 400, such that the first graft portion 409 and the second graft portion 411 can together fit in the cavity 407 (FIG. 1C). The first graft portion 409 and second graft portion 411 span the cavity 407 in posterior-anterior direction and lateral-medial direction interconnecting exposed ramus and mental protuberance of the tissue body 400. Once positioned in the cavity 407, the first graft portion 409 and the second graft portion 411 can be coupled to each other and the tissue body 400.

Bone fixation plates 450 and anchors 470 can be used to couple the graft 408 to the tissue body 400. Bone fixation plates 450 can be used to couple to graft portions to each other and to the tissue body 400. One or more bone bone fixation plates 450 can be placed across the ramus of tissue body 400, the first graft portion 409, the second graft portion 411, and mental protuberance of tissue body 400, then then anchors 450 can be inserted through the bone fixation plates 450 and into the tissue body portions 400 and the graft 408 so as to couple the graft 408 to the tissue body 400. Specifically, the anchors 450 can be inserted into the preformed tissue body bores 430 while other anchors can be inserted through bone plate openings and into corresponding numbers of graft bores 420 formed during resection of the graft 408.

Bone fixation plates 450 can define a plate body extending along a plate longitudinal axis. The plate body defines a plurality of openings extending through the plate along an opening axis such that the opening axis is perpendicular to the plate axis. The openings can be oriented such that the opening axis is angled in any radial direction with respect to the plate axis. The bone plates can include a primary leg and an auxiliary leg obliquely offset relative to the primary leg. The bone fixation plate can define one or more openings in the primary leg and the auxiliary leg. Examples suitable bone fixation plates 460 are described and illustrated in U.S. patent application Ser. No. 12/963,725 filed on Dec. 9, 2010 and published as US Patent Publication No. 2011/0144698 on Jun. 16, 2011, the entire disclosure of which is incorporated by reference herein. Further, the bone fixation plates can be bendable to conform to the anatomy of patient and/or structure of the graft 408. For instance, the bone fixation plate can be bendable, or bent, along one or more portions of the bone fixation plate so that the plate axis aligned with a parallel to the surface of the tissue body 400 and graft 408.

In accordance with alternate embodiments, the bone fixation plates 450 can be patient specific bone plates. For instance, the tissue body 400 prior to resection can be scanned, and the scanned data can be used to develop a virtual three-dimensional model of the tissue body 400 as described above. For instance, Computer Aid Design (CAD) software, running on a computer, can create a virtual three-dimensional model of a bone fixation plate, based on the virtual three-dimensional model of the tissue body. The virtual three-dimensional model of the bone plate can be manipulated or modified, for instance to include holes or openings for receiving anchors therein. The holes can smooth, threaded, or partially threaded and configured to receive an a wide variety of anchors, such as locking screws, compression screws and/or nail and any type of fixation member or device. The plate virtual three-dimensional model can be used to form a patient specific bone plate via rapid processing technologies described herein. For instance, via a computer, the virtual three-dimensional model of the bone plate can be used to develop manufacturing instructions for the bone plate. The manufacturing instructions can be transmitted to a computer in electrical communication with a rapid manufacturing machines. The computer receives the manufacturing instructions, then via a processor, the manufacturing instructions initiate in the rapid manufacturing machine, the formation of the patient specific bone plate. The patient specific bone plate can be formed to have a plurality of openings that are configured to align with the tissue body bores and graft bores. Or, as further detailed below, the resection guide can be manufactured to have drill guides positioned and oriented to align with the openings formed in the patient specific bone plate.

Figure 2A:
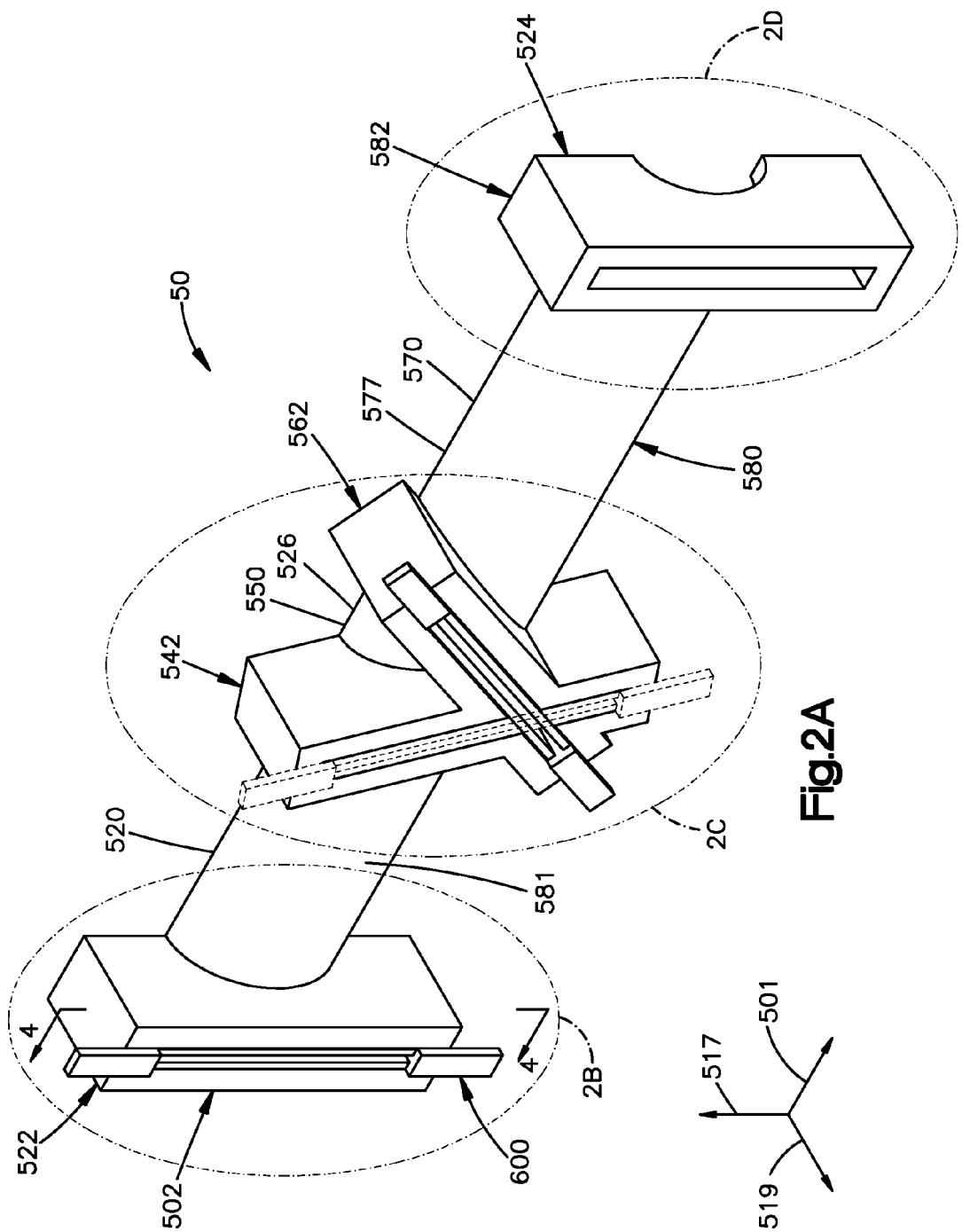
FIG. 2A is a front perspective view of a resection guide of FIG. 1A including a resection guide body and guide members.
Figure 2B:
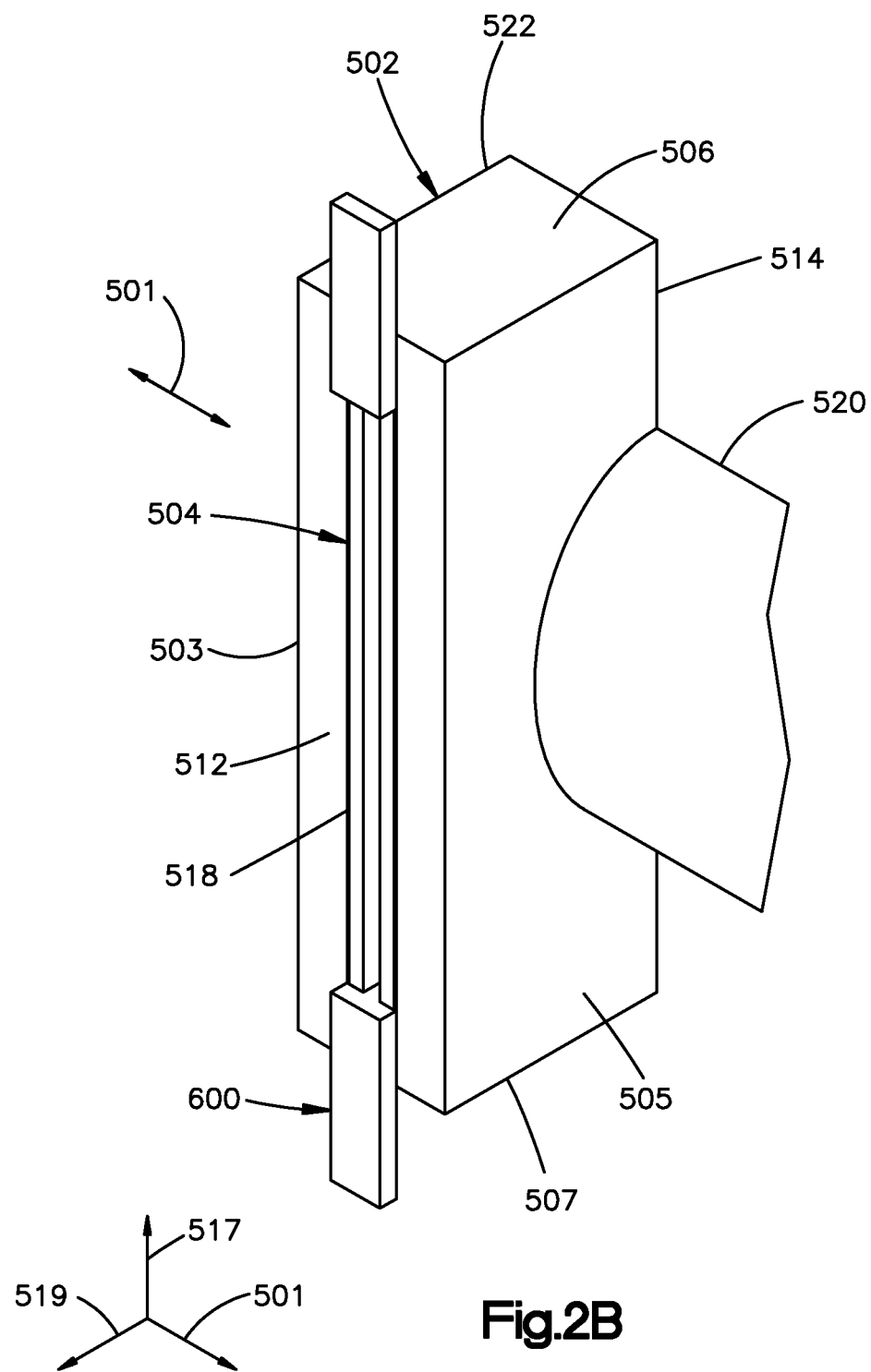
FIG. 2B is an enlarged perspective view of a portion of the resection guide illustrated in FIG. 2A, taken at region 2B and showing a first resection guide supporting member and a first connecting member.

Referring to FIGS. 2A-B, in accordance with an embodiment, the resection guide 50 includes the resection guide body 580 and one or more guide members 60. The resection guide body 580 is configured to support one or more guide members 60, and can be wholly or partly made of a first material, such as any suitable polymeric material. For example, the resection guide body 580 can be at least partially made from the first material. Suitable polymeric materials include, but are not limited to, thermoplastics, thermosets and the like. The material at least partly forming the resection guide body 580 (i.e., the first material) can be a polymeric material to allow the use of a rapid prototyping technology during the manufacturing process, thereby reducing manufacturing cost and streamlining the manufacturing process. For example, the polymeric resection guide body 580 can be manufactured for a specific patient using any suitable rapid prototyping technology. In rapid prototyping manufacturing process, a virtual design, such as a computer aided design model, is transformed into a physical model. Examples of rapid prototyping technologies include, but are not limited to, selective laser sintering (SLS), fused deposition modeling (FDM), stereolithography (SLA), and 3D printing. To take advantage of the rapid prototyping technologies, the first material can have a relatively low hardness. For example, the first material can have a Brinell hardness ranging between about 1 HBS 10/100 and about 3 HBS 1/100. The guide members 60 can be entirely or partly made of a second material, such as any suitable metallic material. Suitable metallic materials include, but are not limited, to stainless steel and aluminum. The second material can have a Brinell hardness ranging between 10 HB and about 200 HB. For example, the second material can have a Brinell hardness of about 120 HB. The guide members 60 can also be referred to as inserts.

With continuing reference to FIG. 2A, the resection guide body 580 defines a first end 522, a second end 524 opposite to the first end 522, and a central portion 526 that is disposed between the first end 522 and the second end 524. The first end 522 is spaced apart from the second end 524 along the longitudinal direction 501. The resection guide body 580 can define an upper body surface 581 and a lower body surface 577 that is opposite the upper body surface. The upper body surface 581 can be spaced from the lower body surface 577 along a transverse direction 519. The lower body surface 577 can be configured and positioned to be placed against the graft source 403. In the depicted embodiment, the resection guide body 580 includes a first resection guide supporting member 502, a second resection guide supporting member 542, a third resection guide supporting member 562, and a fourth resection guide supporting member 582. It is envisioned, however, that the resection guide body 580 can include more or fewer resection guide supporting members. The first resection guide supporting member 502 can be disposed at or near the first end 522 of the resection guide body 580. The second and third resection guide supporting members 542 and 562 can be disposed at or near the central portion 526 of the resection guide body 580. The fourth resection guide supporting member 582 can be disposed at or near the second end 524 of the resection guide body 580.

With continuing reference to FIG. 2A, the resection guide body 580 can include a plurality of connecting members that are configured to couple the resection guide supporting members 502, 542, 562, and 582 to one another. In the depicted embodiment, the resection guide body 580 includes a first connecting member 520, a second connecting member 550, and a third connecting member 570 that are separated from one another along the longitudinal direction 501. The first connecting member 520 can couple the first resection guide supporting member 562 with the second resection guide supporting member 542 such that the first resection guide supporting member 562 and the second resection guide supporting member 542 are spaced apart from each other a predetermined distance along the longitudinal direction 501. A second connecting member 550 can couple the second resection guide supporting member 542 with the third resection guide supporting member 562. A third connecting member 570 can couple the third resection guide supporting member 562 with the fourth resection guide supporting member 582 such that the third resection guide supporting member 562 and the fourth resection guide supporting member 582 are spaced apart from each other a predetermined distance along the longitudinal direction 501. The cross-section of the connecting members 520, 550, and 570 can have any suitable shape. For example, the cross-section of one or more connecting members 520, 550, or 570 can be substantially arc-shaped. It is envisioned, however, that the cross-section of one or more connecting members 520, 550 or 570 can have other suitable shapes, such as circular, oval, rectangular, polygonal, etc. The resection guide supporting members 502, 642, 562, 582 and the connecting members 520, 550, and 570 cooperate to define the resection guide body 580.

With continuing reference to FIG. 2B, the first resection guide supporting member 502 can include a first left side wall 503, a first right side wall 505 opposite to the first left side wall 503, a first front wall 506, and a first rear wall 507 opposite to the first front wall 506. The first front wall 506 can interconnect the first left side wall 503 and the first right side wall 505. The first rear wall 507 can interconnect the first left side wall 503 and the first right side wall 505. The first left side wall 503 can interconnect the first front wall 506 and the first rear wall 507. The first right side wall 505 can interconnect the first front wall 506 and the first rear wall 507. Furthermore, at least a portion of the first right side wall 505 is directly or indirectly connected to the first connecting member 520. The first left wall 503, first right side wall 505, first front wall 506, and first rear wall 507 cooperate so as to define a first upper surface 512. Moreover, the first left wall 503, first right side wall 505, first front wall 506, and first rear wall 507 cooperate so as to define a first lower surface 514.

With continuing reference to FIG. 2B, the first left wall 503, first right side wall 505, first front wall 506, and first rear wall 507 can cooperate so as to define a substantially or completely enclosed first inner surface 518. Alternatively, the first inner surface 518 is not a substantially or completely enclosed. The first inner surface 518 of the resection guide supporting member 502 defines a first resection guide opening 504 that is configured and sized to receive at least a portion of a guide member 60 as discussed in detail below. The first inner surface 518 is disposed between the first upper surface 512 and the first lower surface 514. The first resection guide opening 504 can extend through the first upper surface 512 and the first lower surface 514 along the transverse direction 519 that is substantially perpendicular to the longitudinal direction 501. In the depicted embodiment, the resection guide opening 504 can have a substantially rectangular cross-section, and can be elongate, for example, along a lateral direction 517 that is perpendicular to the longitudinal direction 501. In other words, the resection guide opening 504 can be elongate, for example, along a direction from the first front wall 506 toward the first rear wall 507.

Figure 2C:
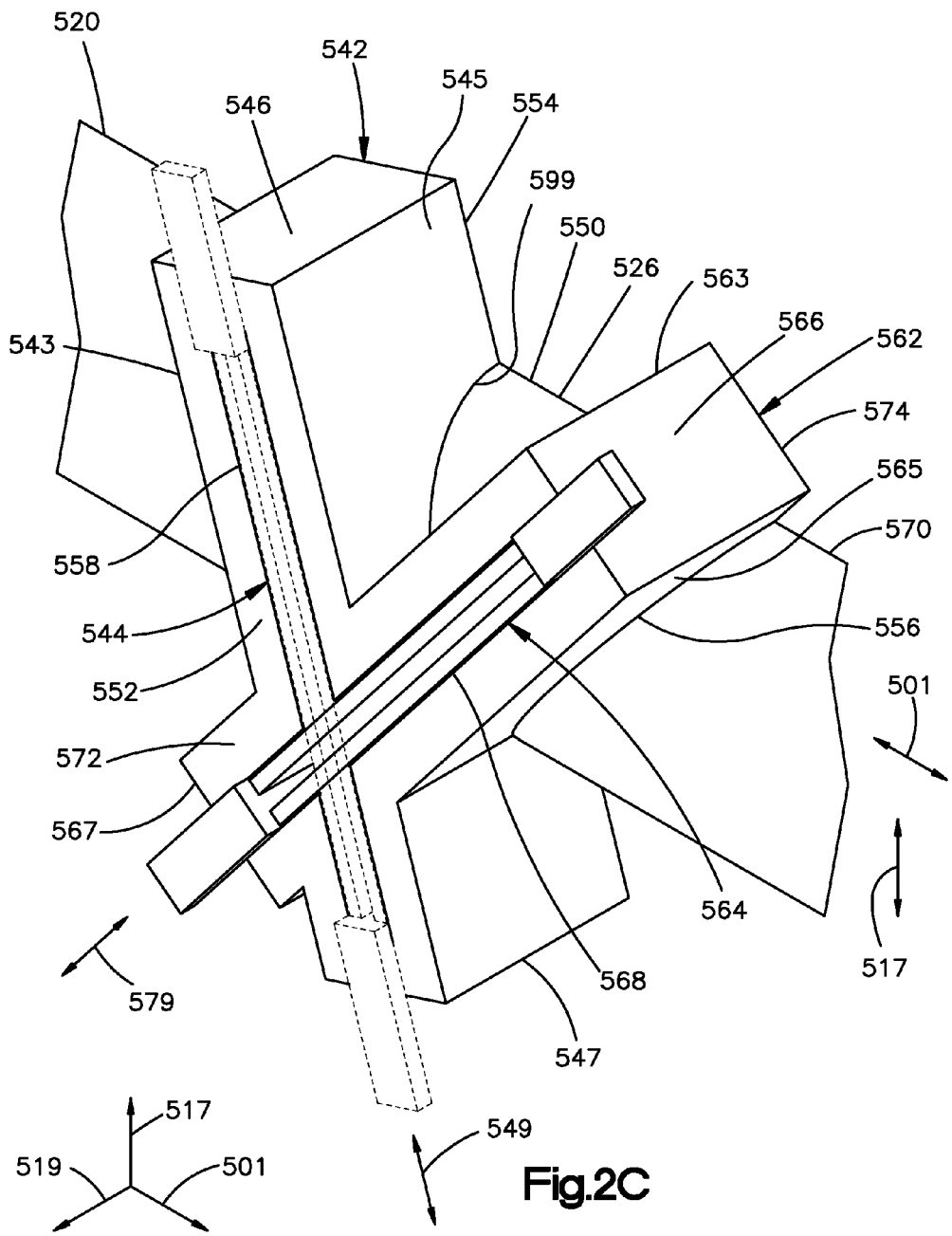
FIG. 2C is an enlarged perspective view of a portion of the resection guide shown in FIG. 2A, taken at region 2C and showing second and third resection guide supporting members, the first connecting member, a second connecting member, and a third connecting member.

Continuing with FIG. 2C, the second and third resection guide supporting members 542 and 526 can be disposed at the central portion 526 of the resection guide body 580. Each of the second and third resection guide supporting members 542 and 562 defines a corresponding resection guide opening 544 and 564. The second and third resection guide supporting members 542 and 562 can be oriented relative to each other so that their respective resection guide openings 544 and 564 intersect each other. The second and third resection guide supporting members 542 and 562 can also intersect each other.

With continuing reference to FIG. 2C, the second resection guide supporting member 542 can include a second left side wall 543, a second right side wall 545 opposite to the second left side wall 543, a second front wall 546, and a second rear wall 547 opposite to the second front wall 546. The second front wall 546 can interconnect the second left side wall 543 and the second right side wall 545. The second rear wall 547 can interconnect the second left side wall 543 and the second right side wall 545. The second left side wall 543 can interconnect the second front wall 546 and the second rear wall 547. The second right side wall 545 can interconnect the first front wall 546 and the second rear wall 547. Furthermore, at least a portion of the second left side wall 543 can be directly or indirectly connected to the first connecting member 520. At least a portion of the second right side wall 545 can be directly or indirectly connected to the second connecting member 550. The second left wall 543, second right side wall 545, second front wall 546, and second rear wall 547 can cooperate so as to define a second upper surface 552. Moreover, the second left wall 543, second right side wall 545, second front wall 546, and second rear wall 547 can cooperate so as to define a second lower surface 554.

Continuing with FIG. 2C, the second left wall 543, second right side wall 545, second front wall 546, and second rear wall 547 can cooperate so as to define a substantially enclosed second inner surface 558. Alternatively, the second inner surface 558 is not a substantially or completely enclosed. The second inner surface 558 of the second resection guide supporting member 542 can define the second resection guide opening 544 that is configured and sized to receive at least a portion of the guide member 60 or any other suitable guide member as discussed in detail below. The second resection guide opening 544 can extend through the second upper surface 552 and the second lower surface 554 along the transverse direction 519. In the depicted embodiment, the resection guide opening 544 can have a substantially rectangular cross-section, and can be elongate, for example, along a first angled direction 549 that defines an oblique angle relative to the longitudinal direction 501. The first angled direction 549 can also define an oblique angle relative to the lateral direction 517. The second resection guide opening 544 can be elongate, for example, along a direction from the second front wall 546 toward the first rear wall 547.

Continuing with FIG. 2C, the third resection guide supporting member 562 can include a third left side wall 563, a third right side wall 565 opposite to the third left side wall 563, a third front wall 566, and a third rear wall 567 opposite to the third front wall 566. The third front wall 566 can interconnect the third left side wall 563 and the third right side wall 565. The third rear wall 567 can interconnect the third left side wall 563 and the third right side wall 565. The third left side wall 563 can interconnect the third front wall 566 and the third rear wall 567. The third right side wall 565 can interconnect the third front wall 566 and the third rear wall 567. Furthermore, at least a portion of the third left side wall 563 can be directly or indirectly connected to the second connecting member 550. At least a portion of the third right side wall 565 can be directly or indirectly connected to the third connecting member 570. The third left wall 563, third right side wall 565, third front wall 566, and third rear wall 566 can cooperate so as to define a third upper surface 572. Moreover, the third left wall 563, third right side wall 565, third front wall 566, and third rear wall 56 can cooperate so as to define a third lower surface 574.

Continuing with FIG. 2C, the third left wall 563, third right side wall 565, third front wall 566, and third rear wall 567 can cooperate so as to define a substantially enclosed third inner surface 568. Alternatively, the third inner surface 568 is not a substantially enclosed. The third inner surface 568 can define the third resection guide opening 564 that is configured and sized to receive at least a portion of the guide member 60 or any other suitable guide member as discussed in detail below. The third resection guide opening 564 can extend through the third upper surface 572 and the third lower surface 574 along the transverse direction 519. In the depicted embodiment, the third resection guide opening 564 can have a substantially rectangular cross-section, and can be elongate, for example, along a second angled direction 579 that defines an oblique angle relative to the longitudinal direction 501. The second angled direction 579 can also define an oblique angle relative to the longitudinal lateral direction 517. The third resection guide opening 564 can be elongate, for example, along a direction from the third front wall 566 toward the first rear wall 567.

Figure 2D:
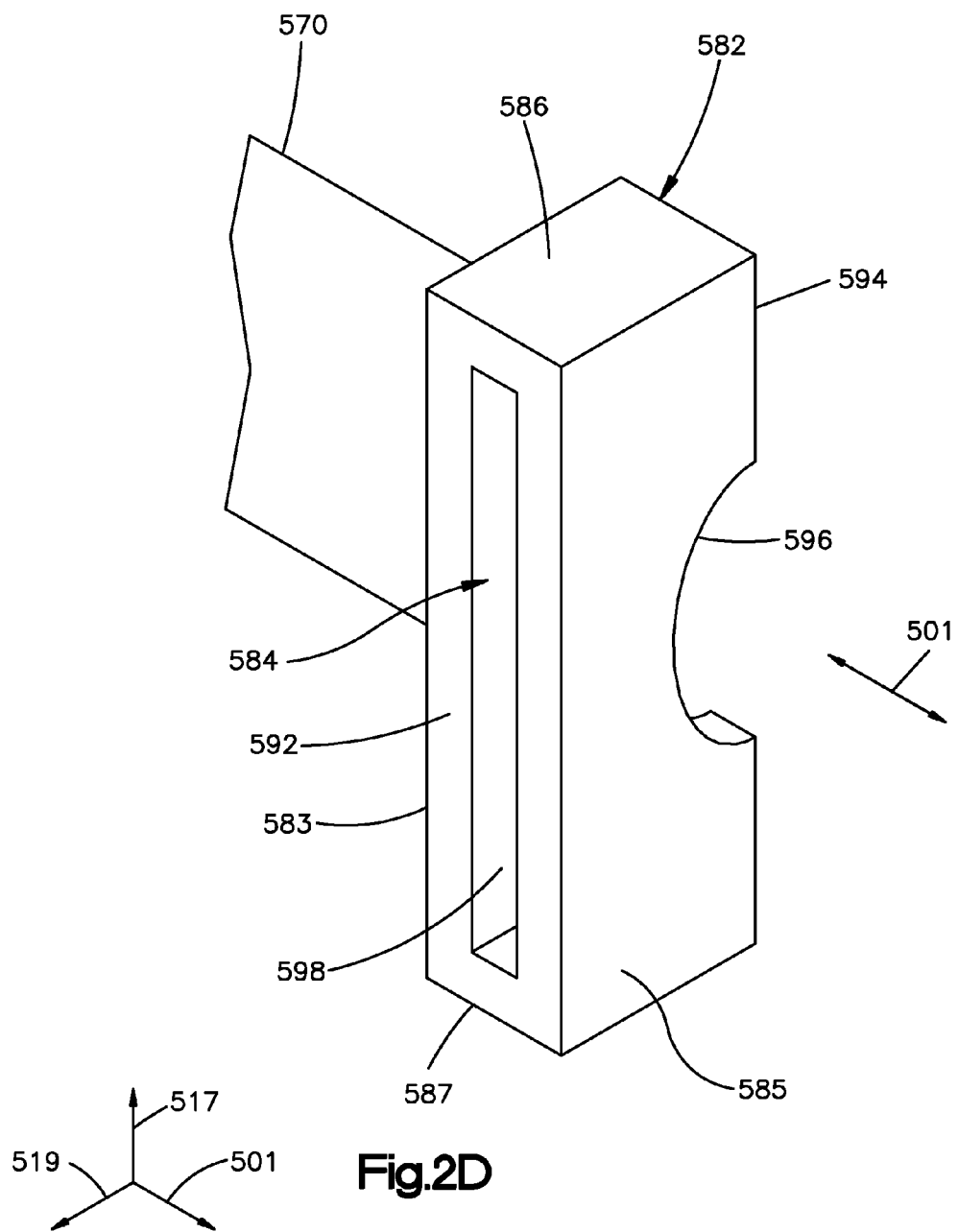
FIG. 2D is an enlarged perspective view of a portion of the resection guide depicted in FIG. 2A, taken at region 2D and showing a fourth resection guide supporting member and the third connecting member.

Referring to FIG. 2D, the fourth resection guide supporting member 582 can be substantially similar to the first resection guide supporting member 502. The fourth resection guide supporting member 582 can include a fourth left side wall 583, a fourth right side wall 585 opposite to the fourth left side wall 583, a fourth front wall 586, and a fourth rear wall 587 opposite to the fourth front wall 586. The fourth front wall 586 can interconnect the fourth left side wall 583 and the fourth right side wall 585. The fourth rear wall 587 can interconnect the fourth left side wall 583 and the fourth right side wall 585. The fourth left side wall 583 can interconnect the fourth front wall 586 and the fourth rear wall 587. The fourth right side wall 585 can interconnect the fourth front wall 586 and the fourth rear wall 587. Furthermore, at least a portion of the fourth left side wall 583 can be directly or indirectly connected to the third connecting member 570. The fourth left wall 583, fourth right side wall 585, fourth front wall 586, and fourth rear wall 586 can cooperate so as to define a fourth upper surface 592. Moreover, the fourth left wall 583, fourth right side wall 585, fourth front wall 586, and fourth rear wall 586 can cooperate so as to define a fourth lower surface 594.

With continuing reference to FIG. 2D, the fourth left wall 583, fourth right side wall 585, fourth front wall 586, and fourth rear wall 586 can cooperate so as to define a substantially or completely enclosed fourth inner surface 598. Alternatively, the fourth inner surface 598 is not a substantially or completely enclosed. The fourth inner surface 598 can define a fourth resection guide opening 584 that is configured and sized to receive at least a portion of the guide member 60 or any other suitable guide member as discussed in detail below. The fourth resection guide opening 584 can extend through the first upper surface 592 and the first lower surface 594 along the transverse direction 519. In the depicted embodiment, the resection guide opening 584 can have a substantially rectangular cross-section, and can be elongate, for example, along the lateral direction 517 that is perpendicular to the longitudinal direction 501. The resection guide opening 584 can be elongate, for example, along a direction from the first front wall 586 toward the first rear wall 587.

Figure 2E:
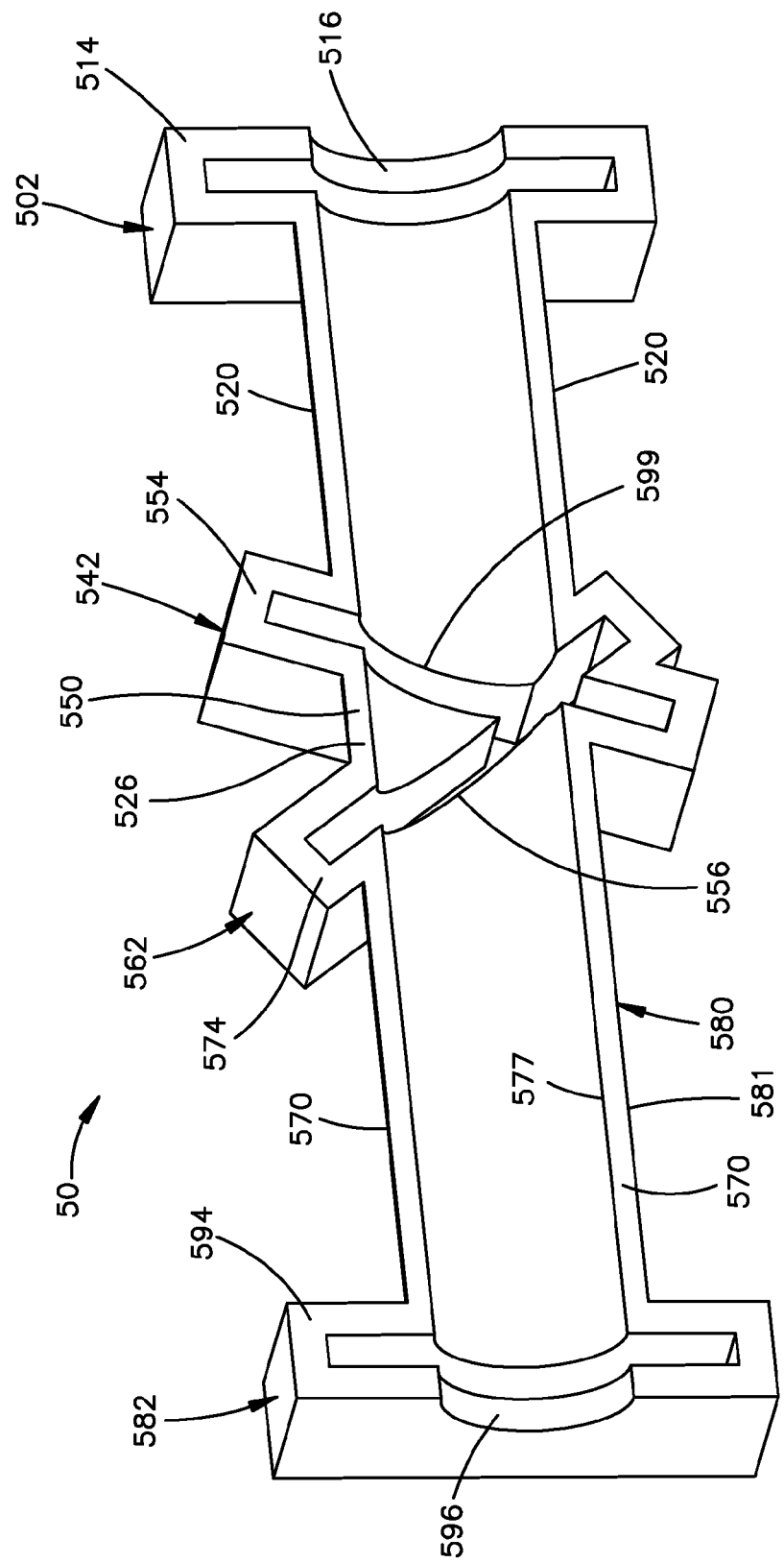
FIG. 2E is a rear perspective view of the resection guide shown in FIG. 2A.

With reference to FIG. 2E, the first lower surface 514 can include a first connecting portion 516 contoured and configured to receive a portion of the tissue body 400 so as to allow the resection guide body 580 to be positioned on a portion of the tissue body 400. The first connecting portion 516 can have a substantially concave shape. The second lower surface 554 can include a second connecting portion 566 contoured and configured to receive a portion of the tissue body 400 so as to allow the resection guide body 580 to be positioned on at least a portion of the tissue body 400. The second connecting portion 566 can have a substantially concave shape. The third lower surface 574 can include a third connecting portion 556 contoured and configured to receive a portion of the tissue body 400 so as to allow the resection guide body 580 to be positioned on at least a portion of the tissue body 400. The third connecting portion 556 can have a substantially concave shape. The fourth lower surface 594 can include a fourth connecting portion 596 contoured and configured to receive a portion of the tissue body so as to allow the resection guide body 580 to be positioned on a portion of the tissue body. The fourth connecting portion 596 can have a substantially concave shape.

Figure 3:
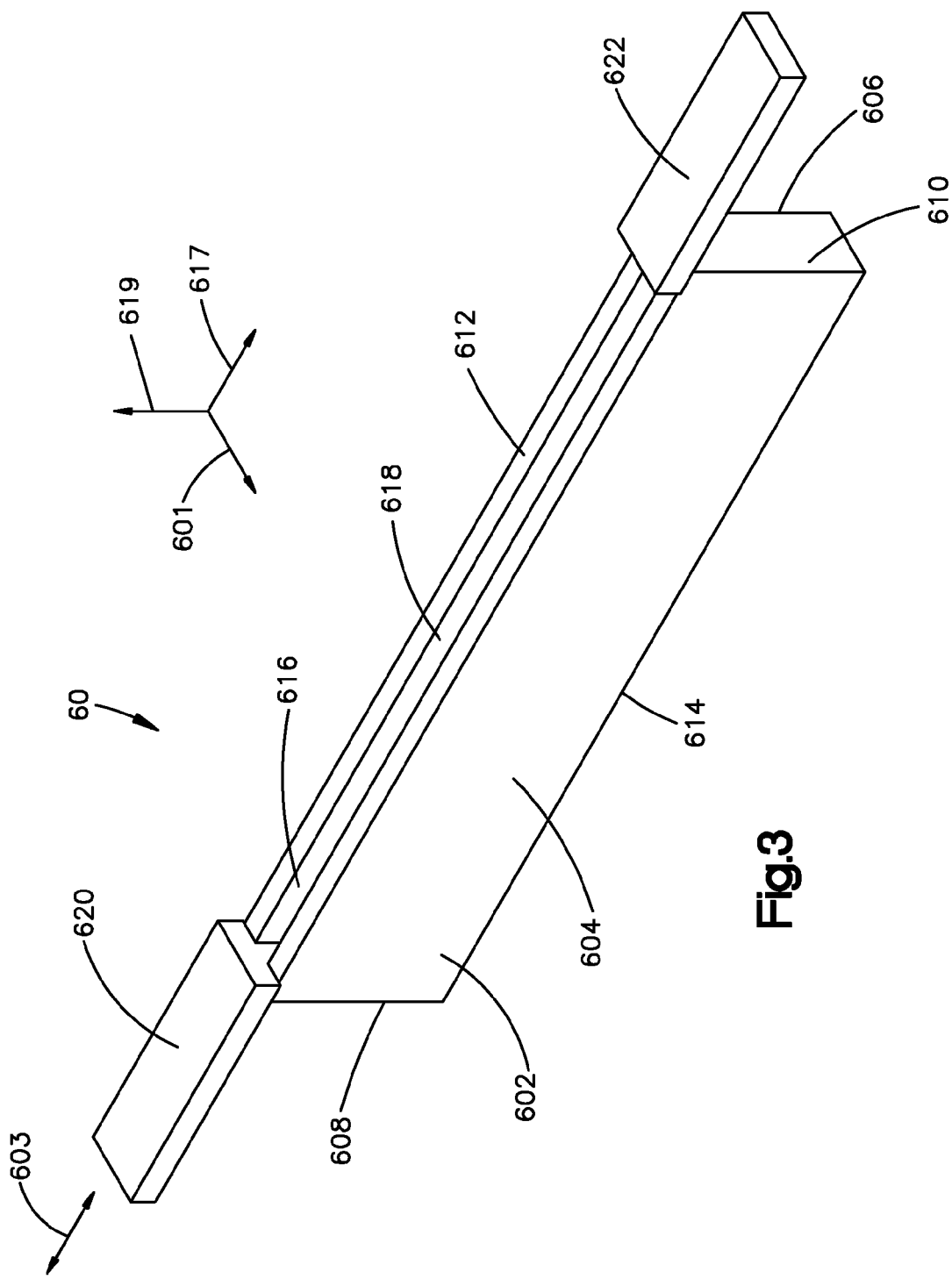
FIG. 3 is a perspective view of the guide member shown in FIG. 2A.
Figure 4:
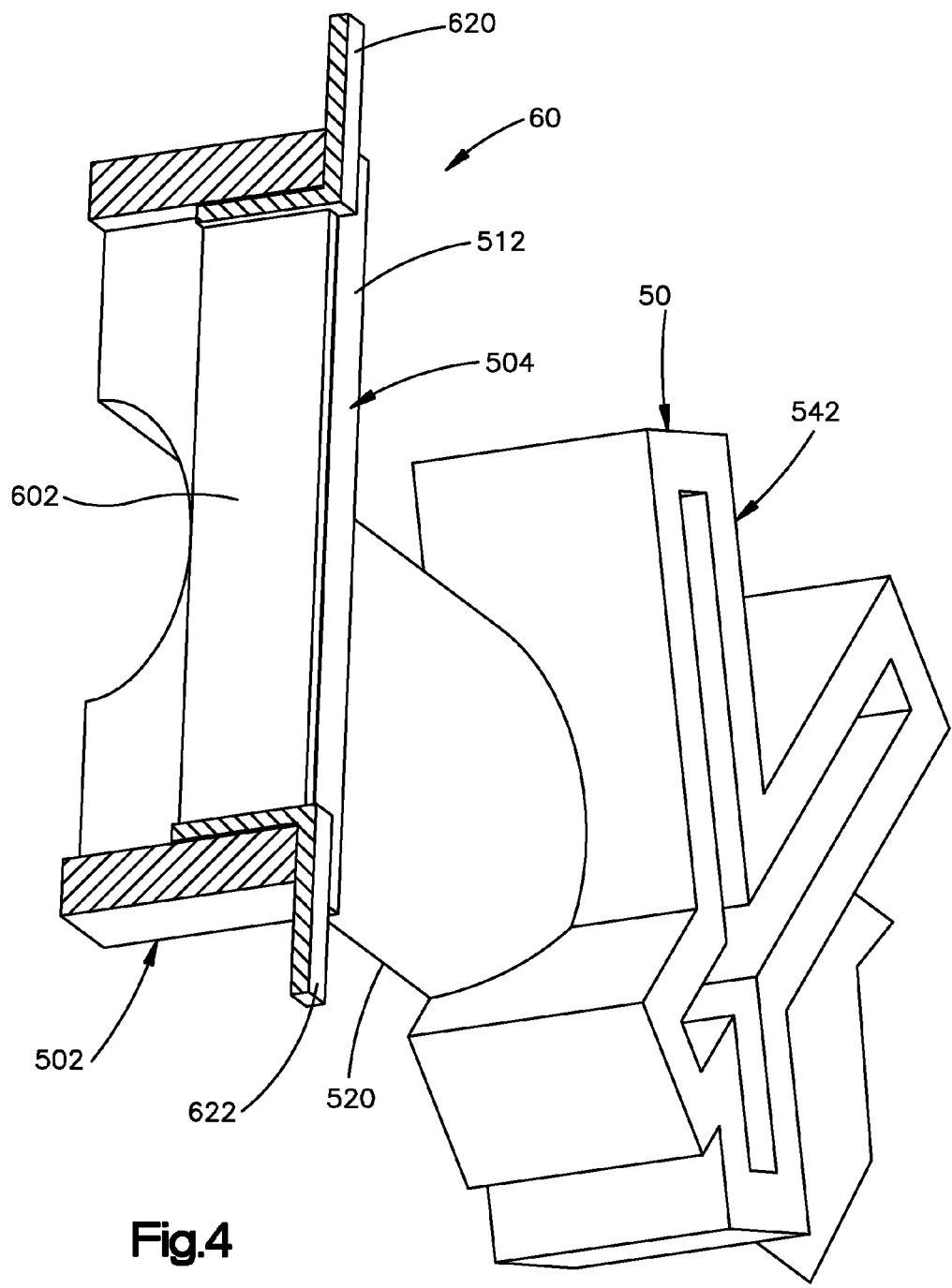
FIG. 4 is a perspective sectional view of the guide member illustrated in FIG. 3 disposed in the first resection guide supporting member illustrated in FIG. 2A, taken along section line 4-4 of FIG. 2A.

Referring to FIGS. 3 and 4, the guide member 60 is configured to guide the resection tool 300 to a desired surgical site in order to make an accurate and precise cut on the tissue body 400. In the depicted embodiment, at least a portion of the guide member 60 is configured and sized to be removably inserted in each of the resection guide openings 504, 544, 564, and 584. For example, the guide member 60 can be configured to be at least partially inserted in at least one of the first resection guide opening 504 or the second resection guide opening 544. At least a portion of the guide member 60 can be removably disposed in the first resection guide opening 504 or the second resection guide opening 544. The guide member 60 can be configured to be selectively inserted into each of the first, second, third, and fourth resection guide openings 504, 544, 564, and 584 so as to guide the resection tool 300 along the graft resection axis 603. Alternatively, the guide member 60 is configured and sized to be removably inserted in some but not all of the resection guide openings 504, 544, 564, and 584.

The guide member 60 can be wholly or partly made of a second material that is different than the first material discussed above. For example, the guide member 60 can be at least partially made of the second material. The second material can be harder than the first material. The second material can be a cut resistant material, such as a metallic material or a ceramic material. As used herein, the term cut resistant material refers to a material that minimizes the wear of the guide member 60 caused by the friction exerted by the resection tool (e.g., a resection tool capable of resecting tissue, such as bone) on the guide member 60 when the resection tool 300 contacts the guide member 106. It is important to employ a cut resistant material because the wear of the guide member 106 may reduce the accuracy of the resection guide 50 and produce wear debris. Wear debris stemming from the resection guide 50 could be detrimental to the long-term efficacy of the bone graft. The second material can be different from the first material, which at least partly forms the resection guide supporting members 502, 542, 562, 582. The hardness of the second material can be greater than the hardness of the first material. For instance, the first material has a first hardness, the second material has a second hardness, and the second hardness is greater than the first hardness. The first material does not necessarily have to be a cut resistant material to minimize costs and streamline the manufacturing process as discussed above. In some embodiments, the second material can have a Brinell hardness that ranges between about 10 HB and about 200 HB. For example, the second material can have a Brinell hardness of about 120 HB. The hardness ranges and values described above are important because a guide member 60 wholly or partly made of a material with these hardness values minimizes the wear of the guide member 60 during use, thereby extending the life of the resection guide 50. The second material can be at least partially made from a laser-sintered metallic material. The second material can be made using a direct metal laser sintering process. As discussed above, the resection guide body 580 can be wholly or partly made of a first material that has a Brinell hardness that ranges between about 1 HBS 10/100 and about 3 HBS 10/100.

With reference to FIGS. 3 and 4, the guide member 60 includes a guide member body 602. The guide member body 602 can be a monolithic (i.e., one-piece) structure or a structure composed of multiple connected parts. In the depicted embodiment, the guide member body 602 can include a guiding left wall 604, a guiding right wall 606 opposite the guiding left wall 604, a guiding front wall 608, and a guiding rear wall 610 opposite to the guiding front wall 608. In other words, the guide member body 602 can define the front wall 608, the rear wall 610 opposite the front wall 608, and a pair of side walls 604 and 606 that extend between the front and rear walls 608 and 610. The front wall 608, the rear wall 610, and the side walls 606 and 604 define the guide member opening 618. The guiding front wall 608 can be spaced apart from the guiding rear wall 610 along a transverse direction 614. The guiding left wall 604 can be spaced apart from the guiding right wall 606 along a longitudinal direction 601. The guiding left wall 604 can interconnect the guiding front wall 608 and the guiding rear wall 610. The guiding right wall 606 can interconnect the guiding front wall 608 and the guiding rear wall 610. The guiding front wall 608 can interconnect the guiding left wall 604 and the guiding right wall 606. The guiding rear wall 610 can interconnect the guiding left wall 604 and the guiding right wall 606.

With reference to FIGS. 3 and 4, the guiding left wall 604, guiding right wall 606, guiding front wall 608, and guiding rear wall 610 can cooperate so as to define a guiding upper surface 612. Furthermore, the guiding left wall 604, guiding right wall 606, guiding front wall 608, and guiding rear wall 610 can cooperate so as to define a guiding lower surface 614. Moreover, the guiding left wall 604, guiding right wall 606, guiding front wall 608, and guiding rear wall 610 can cooperate so to define a guiding inner surface 616. The guiding inner surface 616 can define a guide member opening 618 that can extend through the guiding upper surface 612 and the guiding lower surface 614 along the lateral direction 619. Thus, the guide member 60 can define the guide member opening 618 that extends through the guide member body 602. The guide member opening can be elongate along a graft resection axis 603. The guide member opening 618 is configured and sized to receive at least a portion of the resection tool 300 such that the guide member 60 guides a movement of the resection tool 300 along the graft resection axis 603 when the resection tool 300 is received in the guide member opening 618. The side walls 604 and 606 can be elongate along the graft resection axis 603.

With reference to FIGS. 3 and 4, the guide member 60 further includes at least one tab 620 or 622 that protrudes from the guide member body 602. Each of the tabs 620 and 622 is configured to help retain the guide member 60 in the corresponding resection guide supporting members 502, 542, 562, and 582 as discussed in detail below. In the depicted embodiment, the guide member 60 includes a first tab 620 that can be directly or indirectly connected to the guiding front wall 608, and a second tab 622 that can be directly or indirectly connected to the guiding rear wall 610. The first tab 620 can be at least partially disposed on top of the guiding front wall 608. The second tab 622 can be at least partially disposed on top of the guiding rear wall 610. In some embodiments, the first tab 620 is cantilevered from guiding front wall 608, and the second tab 622 is cantilevered from the guiding rear wall 610. Thus, at least one of the tab 620 or the tab 622 can be cantilevered from the guide member body 602.

When the guide member body 602 is inserted in the resection guide opening 504, 544, 564, or 584, the first tab 620 and second tab 622 are each configured to abut a portion of the upper surface of the corresponding resection guide supporting member 502, 542, 562, or 582 to thereby retain the guide member 60 in the resection guide body 580. For example, the guide member body 602 can be removably inserted in the resection guide opening 504 of the resection guide supporting member 502. When the guide member body 602 is disposed in the resection guide opening 504, the first and second tabs 620 and 622 abut the upper surface 512 of the resection guide body 504 to thereby retain the guide member 60 in the resection guide supporting member 502. At least one of the tab 620 or the tab 622 can be configured to abut at least a portion of the upper body surface 581 when the guide member body 602 is fully seated into the first resection guide opening 504 or the second resection guide opening 544. The guide member 60 can include the second tab 622 that is cantilevered from the guide member body 602. The second tab 622 can be configured to abut at least a portion of the upper body surface 581 when the guide member body 602 is fully seated in the first resection guide opening 504 or the second resection guide opening 544. The first tab 620 can protrude from the front wall 608, and the second tab 622 can protrude from the rear wall 606.

Figure 5:
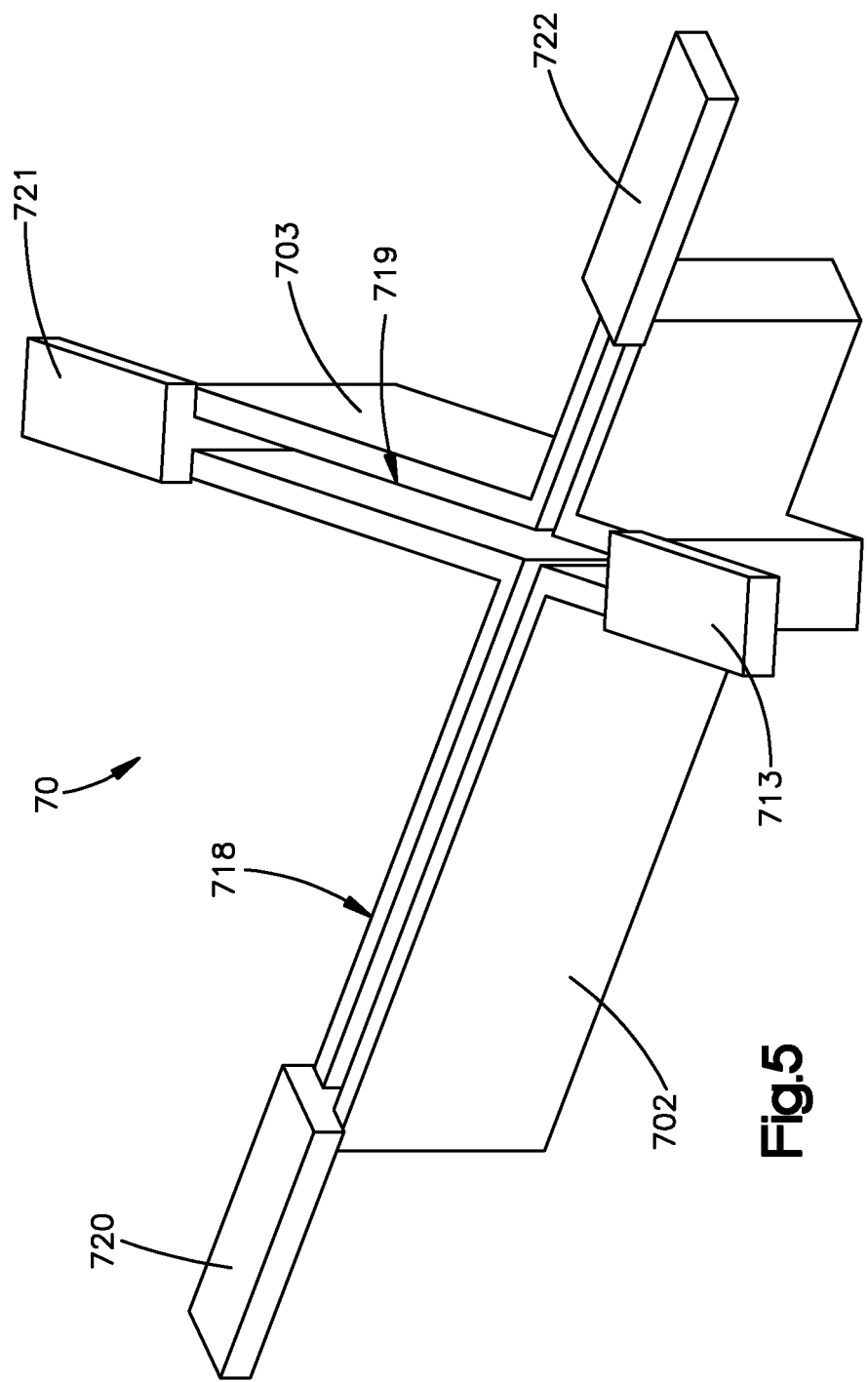
FIG. 5 is a perspective view of a guide member in accordance to another embodiment of the present disclosure.

With reference to FIG. 5, a guide member 70 is configured to be simultaneously disposed in the resection guide supporting members 542 and 562. The guide member 70 is substantially similar to the guide member 60, except that the guide member 70 includes two guide member bodies instead of one guide member body. The guide member 70 includes a first guide member body 702 and a second guide member body 703 that intersect each other. The first and second guide member bodies 702 and 703 are oriented such that they are configured to be disposed simultaneously in the resection guide openings 544 and 564. For example, the first guide member body 702 can be disposed to be removably inserted in the resection guide opening 544, while the second guide member body 703 can be configured to be removably disposed in the resection guide opening 564. Each of the guide member bodies 702 and 703 can define a respective guide member opening 718 and 719 that is configured and sized to receive at least a portion of the resection tool 300 to thereby guide the movement of the resection tool 300 toward the tissue body 400. The guide member openings 718 and 719 can intersect each other. The guide member 70 can further include at least one tab 720 that protrudes from the respective guide member bodies 702 and 703. In the depicted embodiment, the guide member body 702 can include a first tab 720 and a second tab 722. Similarly, the guide member body 703 can include a first tab 721 and a second tab 723. The guide member 70 can be wholly or partly made of the second material discussed above. The second material can be a cut resistant material, such as a metallic material or a ceramic material.

In operation, the user positions the resection guide supporting members 502, 542, 562, and 582 in the desired location adjacent to the tissue body 400 (FIG. 1A). Then, the guide member 60 is inserted in a resection guide opening 504, 544, 564 or 584 to couple the guide member 60 to the corresponding the resection guide supporting member 502, 542, 562, or 582. Next, at least a portion of the resection tool 300 is inserted through the guide member opening 618. The resection tool 300 is advance toward the tissue body 400 to make a precise cut of the tissue body 400. The guide member 60 can then be removed from the resection guide body and inserted in another resection guide body. In addition, the user can place guide member 70 in the resection guide openings 544 and 564. The resection tool 300 can then be inserted and advanced through the guide member opening 718 to make a first cut on the tissue body 400. Moreover, the resection tool 300 can also be inserted in the guide member opening 719 to make another cut on the tissue body 400.

Figure 6A:
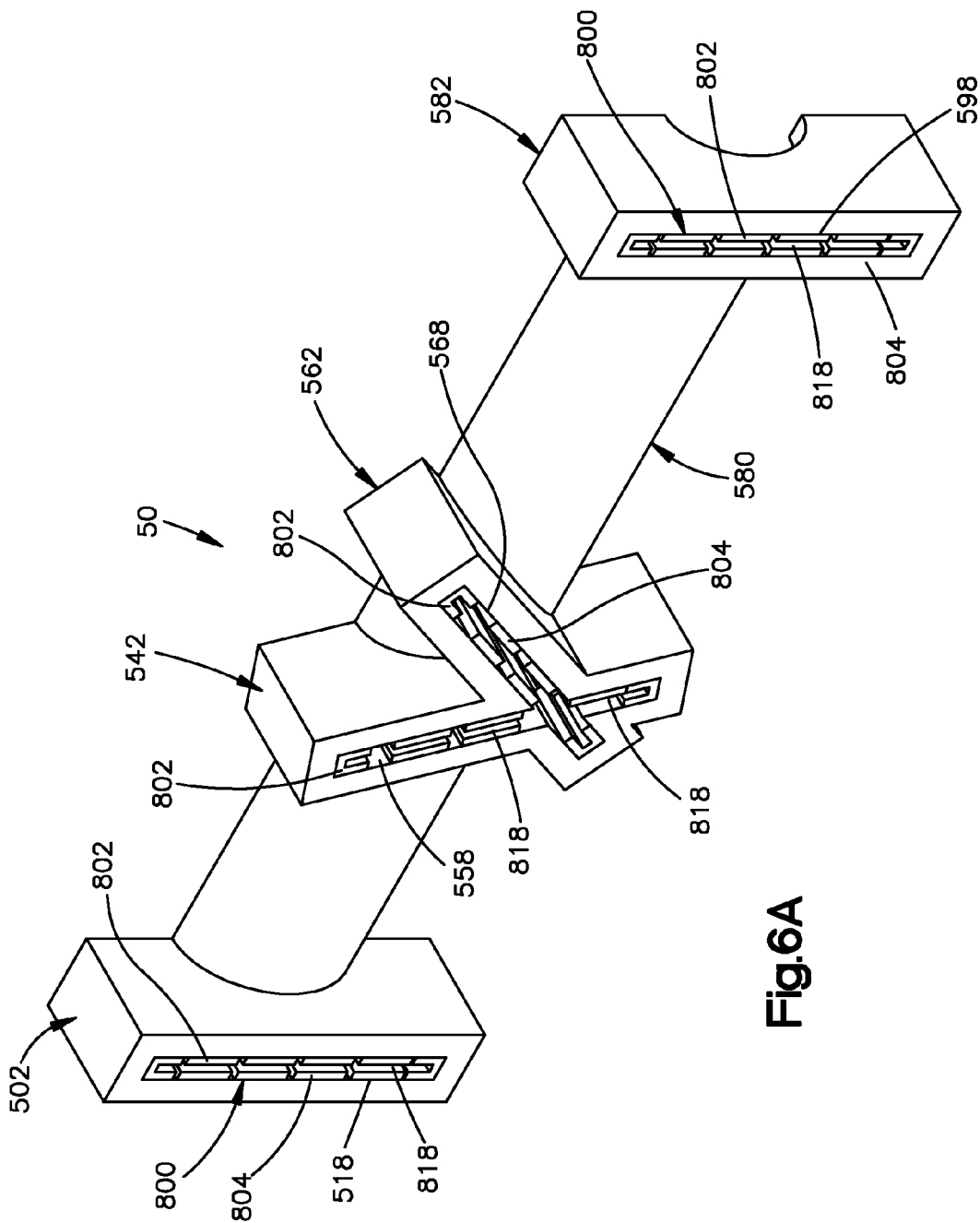
FIG. 6A is a perspective view of a resection guide in accordance with an embodiment of the present disclosure that includes a resection guide body and discrete guiding components.

With reference to FIG. 6A, in accordance with an alternate embodiment, the resection guide 50 can include guide members 800 formed by a plurality of discrete guiding components 802, such as discrete guiding inserts. As used herein, the term "discrete components" refers, for example, to unconnected elements. Like in other embodiments, the discrete guiding components 802 can be entirely or partly made from a cut resistant material (e.g., the second material discussed above). The discrete guiding components 802 can be made from the second material. The discrete guiding components 802 can be attached to the first inner surface 518, second inner surface 558, third inner surface 568, and fourth inner surface 598. For instance, when the discrete guiding components 802 are attached to the first inner surface 518, second inner surface 558, third inner surface 568, and fourth inner surface 598, the discrete guiding components 802 can cooperate to define a guide member opening 818 that is configured and sized to receive at least a portion of the resection tool 300 to thereby guide the movement of the resection tool 300 toward the tissue body 400. The resection guide body 580 can includes the first and second inner surfaces 518, 558 that at least partially define the first and second resection guide openings 504, 544, respectively, and guide member 60 is segmented so as to define a plurality of discrete guiding components 802 that are configured to be mounted to at least one of the first or second inner surfaces 518, 558.

With continuing reference to FIG. 6A, the discrete guiding component 802 can be attached to the resection guide supporting members 502, 542, 562, 582 along the respective first inner surface 518, second inner surface 558, third inner surface 568, and fourth inner surface 598. In the depicted embodiment, the discrete guiding components 802 can include at least one guiding wall 804. The guiding wall 804 can have a substantially planar configuration.

Figure 6B:
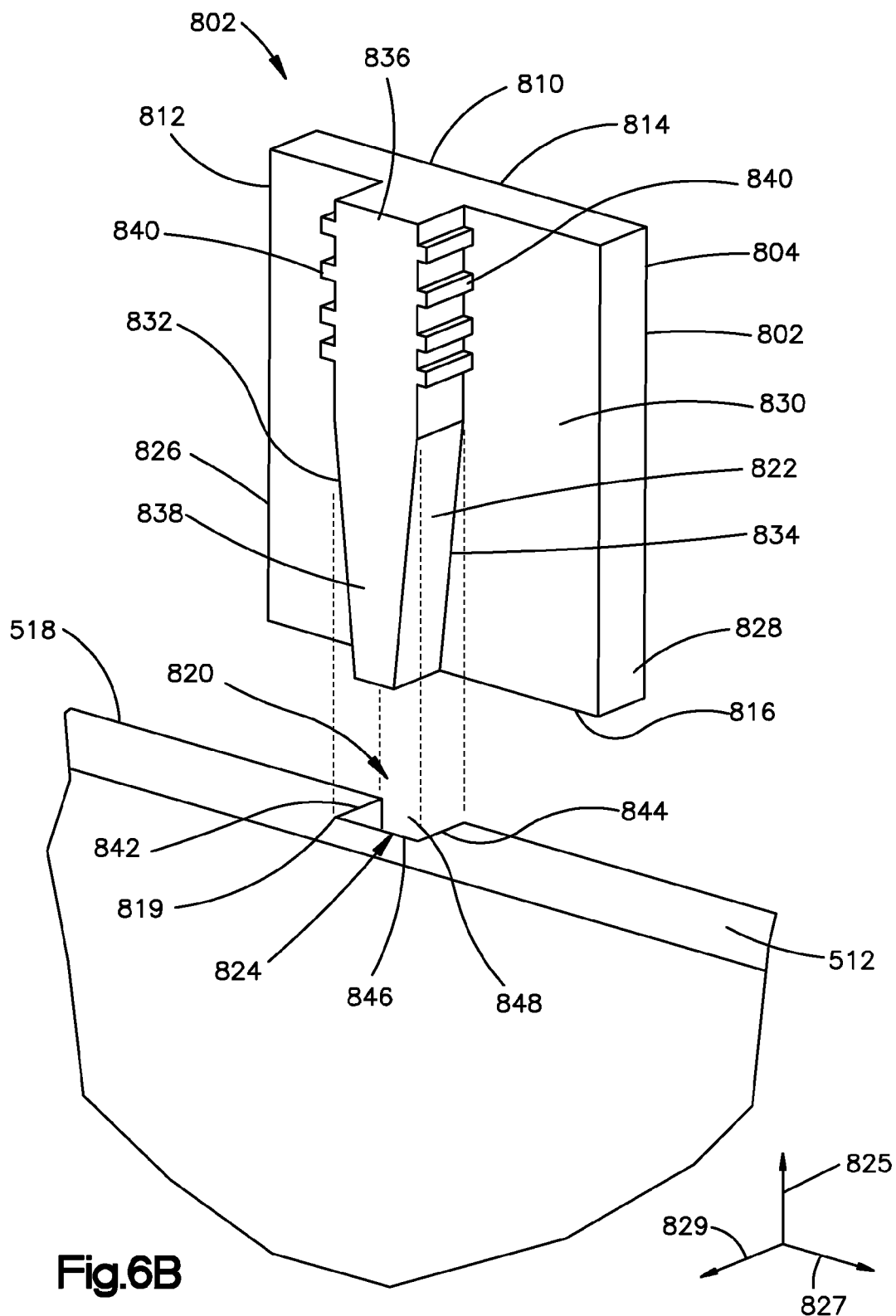
FIG. 6B is an enlarged perspective view of a portion of the resection guide shown in FIG. 6A and one discrete guiding component being coupled to the resection guide body.

With continuing reference to FIG. 6B, any of the discrete guiding components 802 described above can be attached to the first inner surface 518, second inner surface 558, third inner surface 568, or fourth inner surface 598 by any suitable apparatus, connection, or mechanism. For example, a press-fit connection 820 can be used to attach a discrete component 802 to the first inner surface 518 (or any other inner surface) of the resection guide supporting member 502 (or any other resection guide body). In the interest of brevity, the present disclosure describes the connection between the discrete guide member 802 and the first resection guide supporting member 502; however, the discrete guide member 802 can be connected to any of the resection guide supporting members as described below. The press-fit connection 820 includes a first engagement member 822 and a second engagement member 819. The discrete guiding components 802 and the respective first or second inner surface 518 or 558 defines complementary engagement members 822 and 819 that are configured to mate so as to attach the discrete guiding components 802 to the respective inner surface 518 and 558. The first engagement member 822 can be part of the discrete guiding component 802, and the second engagement member 819 can be part of the resection guide supporting member 502 (or any other resection guide body of the resection guide body 580). The first engagement member 822 is configured to engage the second engagement member 819 so as to connect the discrete guide member 802 to the resection guide supporting member 502. The second engagement member 819 can include a groove 824 that extends into the inner surface 518 and is configured to receive at least a portion of the engagement member 822. Thus, the inner surface 518 (or 558 or any other inner surface of the resection guide body 580) can define the groove 824 that is configured to receive the tongue 830. The tongue 830 can be tapered so as to so as to be press-fit within the respective groove 824.

With continuing reference to FIG. 6B, as discussed above, each discrete guiding component 802 includes at least one guiding wall 804. The guiding wall 804 can define an outer surface 810, an inner surface 812 opposite to the outer surface 810, an upper surface 814, a bottom surface 816 opposite the upper surface 814, a first sidewall 826, and a second sidewall 828 opposite the first sidewall 826. The outer surface 810 is spaced from the inner surface 812 along a lateral direction 829. The upper surface 814 is spaced from the bottom surface 816 along a transverse direction 825 that is substantially perpendicular to the lateral direction 829. The first side wall 826 is spaced from the second sidewall 828 along a longitudinal direction 827 that is substantially perpendicular to the lateral direction 829. The longitudinal direction 827 can also be substantially perpendicular to the transverse direction 825.

With continuing reference to FIG. 6B, the first engagement member 822 can be a protrusion 823 that protrudes from the guiding wall 804. In the depicted embodiment, the first engagement member 822 can protrude from the guiding wall 804 in a direction away from the inner surface 812 along the lateral direction 829. The first engagement member 822 is coupled to the inner surface 812, and can be elongate in a direction from the upper surface 814 toward the bottom surface 816. In the depicted embodiment, the first engagement member 822 can be elongate along the transverse direction 825. The first engagement member 822 can be monolithically formed with the guiding wall 804, and can be shaped as a column. Furthermore, the first engagement member 822 of each of the discrete guiding components 802 can include a tongue 830 that defines a first sidewall 832 and a second sidewall 834 opposite to the first sidewall 832. The first sidewall 832 is spaced from the second sidewall 834 along the longitudinal direction 827. The tongue 830 includes an upper portion 836 and a lower portion 838. The upper portion 836 is located closer to the upper surface 814 than the lower portion 838. The lower portion 838 is located closer to the bottom surface 816 than the upper portion 836. The tongue 830 has a width defined from the first sidewall 834 to the second sidewall 832. The lower portion 838 can have a tapered configuration such that the width of the tongue 830 decreases in a direction from upper surface 814 toward the bottom surface 816. (i.e., downwardly). The tapered configuration of the lower portion 838 facilitates insertion of the first engagement member 822 into the groove 824.

With continuing reference to FIG. 6B, the first engagement member 822 further includes one or more projections 840, such as barbs, that protrude from the tongue 830. In the depicted embodiment, a plurality of projections 840 are disposed along the first and second sidewalls 832 and 834 at the upper portion 836. Alternatively, the surfaces defining the groove 824 can include protrusions that are configured to be received inside recesses defined by the first engagement member 822.

As discussed above, the second engagement member 819 can be the groove 824 that is configured and sized to receive the guiding connection member 822. The groove 824 can extends into the first inner surface 518 and is configured to receive at least a portion of the first engagement member 822. The mounting channel 822 can be defined by a first sidewall 842, a second sidewall 844 opposite to the first sidewall 842, and an end wall 846. The first sidewall 842 can be spaced from the second sidewall 844 along the longitudinal direction 827. In addition, the mounting channel 822 can define an open end 848 to facilitate insertion of the first engagement member 822 in the mounting channel 822. The open end 848 is located along the upper surface 512 of the resection guide supporting member 502 (or other upper surface of another resection guide body). The mounting channel 822 can define another open end along first lower surface 514 (or other lower surface of another resection guide body). Moreover, the mounting channel 822 can be elongate in a direction from the upper surface 512 toward the lower surface 514 (i.e., along the transverse direction 825). The width of first engagement member 822 at the upper portion 836 is sufficiently large so that the projections 840 contact at least one of the first sidewall 842 or the second sidewall 844 when the upper portion 836 is at least partially disposed in the mounting channel 822 to thereby secure the first engagement member 822 to the second engagement member 819. The secure connection between the first engagement member 822 and the second engagement member 819 in turn causes the discrete guiding component 802 to be connected to the resection guide supporting member 502.

With continuing reference to FIG. 6B, the discrete guiding component 802 can be coupled to the resection guide supporting member 502 (or any other resection guide supporting member) by inserting the first engagement member 822 into the groove 824. The lower portion 838 can be inserted first, and then the first engagement member 822 can be advanced further into the groove 824 until at least one projection 840 contacts the first sidewall 842 or second sidewall 844 that define the mounting channel 822. The friction created between the projections 840 and at least one of the first sidewall 842 or second sidewall 844 when at least a section of the upper portion 836 is disposed in the mounting channel 822 causes the discrete guiding component 802 to be secured to the resection guide supporting member 502 (or any other resection guide supporting member).

Figure 7:
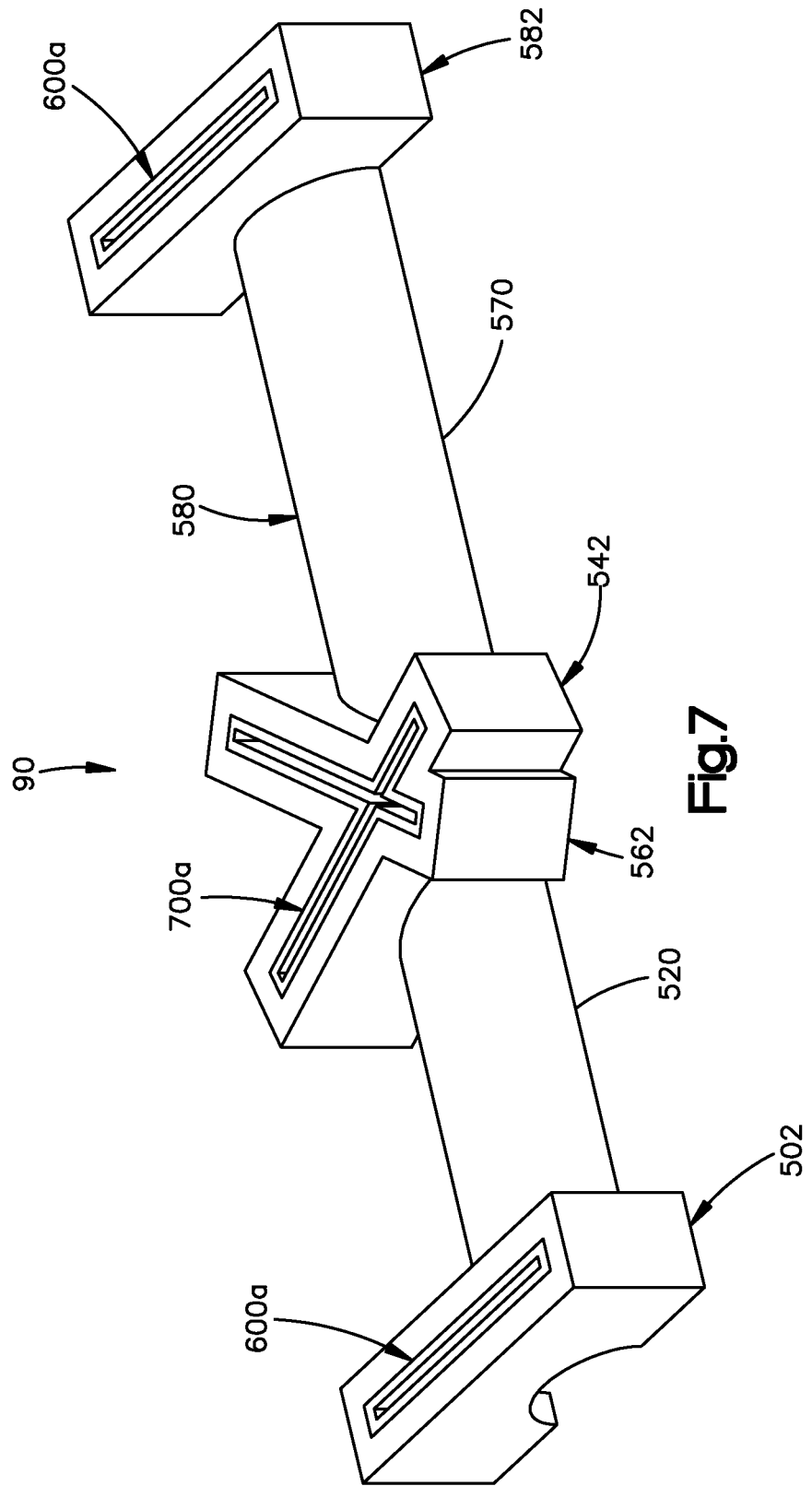
FIG. 7 is a perspective view of a resection guide in accordance with an embodiment of the present disclosure.

With reference to FIG. 7, a resection guide 90 is substantially similar to the resection guide 50 shown in FIG. 2A. However, in this embodiment, the resection guide support 580 is wholly or partly made of a laser sintered polymer material, and the guide members 60a and 70a are entirely or partly made of a laser sintered metallic material. The resection guide support 580 can be manufactured using a direct metal laser sintering (DMLS) process, whereas the guide members 60a and 70a can be manufactured using stereolithography (commonly referred to as SLA). The DMLS and SLA processes allow 3D CAD drawings to be turned into physical objects, thereby facilitating and streamlining the manufacturing process. The guide members 60a are substantially similar to the guide member 60 shown in FIG. 13. However, the guide member 60a does not necessarily include supporting members and are not necessarily configured to be removed from the resection guide supporting members 502 and 582. For example, the guide members 60a can be press fitted into the resection guide supporting members 502 and 582. The guide member 70a is substantially similar to the guide member 70 shown in FIG. 5. However, the guide member 70a does not necessarily include supporting members and are not necessarily configured to be removed from the resection guide bodies 542 and 562. For instance, the guide member 70a can be press fitted into the resection guide bodies 542 and 562. As with the other guide members described above, the guide members 60a and 70a are wholly or partly made from a cut resistant material, such as a metallic material.

With reference to FIG. 8, a resection guide 1000 is substantially similar to the resection guide 50 shown in FIG. 2A, but does not necessarily include guide members. The resection guide 1000 is entirely or partly made of a cut resistant material, such as a metallic material. For instance, the entire resection guide 100 can be manufactured from a metallic material using a direct metal laser sintering (DMLS) process. As discussed above, in the DMLS process, 3-D CAD drawings can be turned into physical objects.

With continuing reference to FIG. 8, the resection guide 1000 can include metallic resection guide body 1080. The resection guide body 1080 can define an upper body surface 1081 and a lower body surface 1077 opposite the upper body surface 1081. The lower body surface 1077 can be configured to face the graft source 403. The resection guide body 1080 can define a first and second resection guide openings 1004 and 1044 that are spaced from each other and extend from the lower body surface 1077 through the upper body surface 1081. The first and second resection guide openings 1004 and 1044 can define respective first and second graft resection axes 1091 and 1093 that are configured to receive a portion of the resection tool 300 and guide the resection tool 300 along the respective first and second resection guide openings 1004 and 1044 so as to resect a graft portion from the graft source 403. The resection guide body 1080 can define a third and fourth resection guide openings 1064 and 1084 that are spaced from each other and extend from the lower body surface 1077 through the upper body surface 1081. The third and fourth resection guide openings 1064 and 1084 can define respective third and fourth graft resection axes 1095 and 1097 that are configured to receive a portion of the resection tool 300 and guide the resection tool 300 along the respective first and second resection guide openings 1064 and 1084 so as to resect a graft portion from the graft source 403. The resection guide body 1080 can define first and second inner surfaces 1018 and 1058 that at least partially define the first and second resection guide openings 1004 and 1044. The first and second inner surfaces 1018 and 1058 are configured to contact the resection tool 300 as the resection tool 300 is guided along the respective first and second graft resection axes 1091 and 1093. The resection guide body 1080 can define third and fourth inner surfaces 1068 and 1098 that at least partially define the first and second resection guide openings 1064 and 1084. The third and fourth inner surfaces 1068 and 1098 are configured to contact the resection tool 300 as the resection tool 300 is guided along the respective first and second graft resection axes 1095 and 1097. The openings 1004, 1044, 1064, and 1084 can be devoid of inserts that are discrete with the resection guide body 1080. The metallic resection guide body 1080 can be laser-sintered. The first and second axis 1091 and 1039 can be angularly offset with respect to each other. The third and fourth exes 1095 and 1097 can be angularly offset with respect to each other. The resection guide body 1080 can be made from a metallic material that has a Brinell hardness ranging between about 10 HBS and about 200 HBS. For example, the resection guide body 1080 can be made from a metallic material that has a Brinell hardness of about 120 HB.

Referring to FIG. 9A, the resection guide 110 includes a resection guide body 580 that defines one or more resection guides and/or resection support members as described above. In accordance with the alternative embodiment, the resection guide 110 can include and one or more drilling guide members 900. The resection guide 110 can be a patients specific resection guide, designed and manufactured as described above in other embodiments of the present disclosure. The resection guide 110 is configured to be placed on the graft source 403 such that the resection guide members are in alignment with resection axes (FIG. 1A), while the drilling guide members 900 align with desired anchor locations on the graft source 403. Anchor locations are locations on the graft source 403 that are suitable for securing a bone fixation plate thereto when graft 408 is positioned on the tissue body 400. As discussed above, the resection guide 110 is patient specific; the resection guide members guide a cutting tool 300 to the graft source 403 so as to cut patient specific graft portions 409 and 411, and the drilling guide members 900 guide a drill bit 310 to the graft source 403 to form patient specific graft bores 420 at the desired anchor locations. The graft bores 420 are formed in the graft source 403 during resection so that when the graft 408 is positioned in the cavity 407, and the fixation plate 450 is placed against the graft 408 and tissue body 400, one or more of graft bores 420 are aligned with a corresponding number of holes in the fixation plate 450. An anchor 460 can be interested through the hole in the bone fixation plate 450 into the aligned graft bore 420. It should be appreciated that the graft bores 420 can be formed at any location the graft source 403 depending on the configuration of the resection guide and drill guide members 900, as further described below.

Figure 9B:
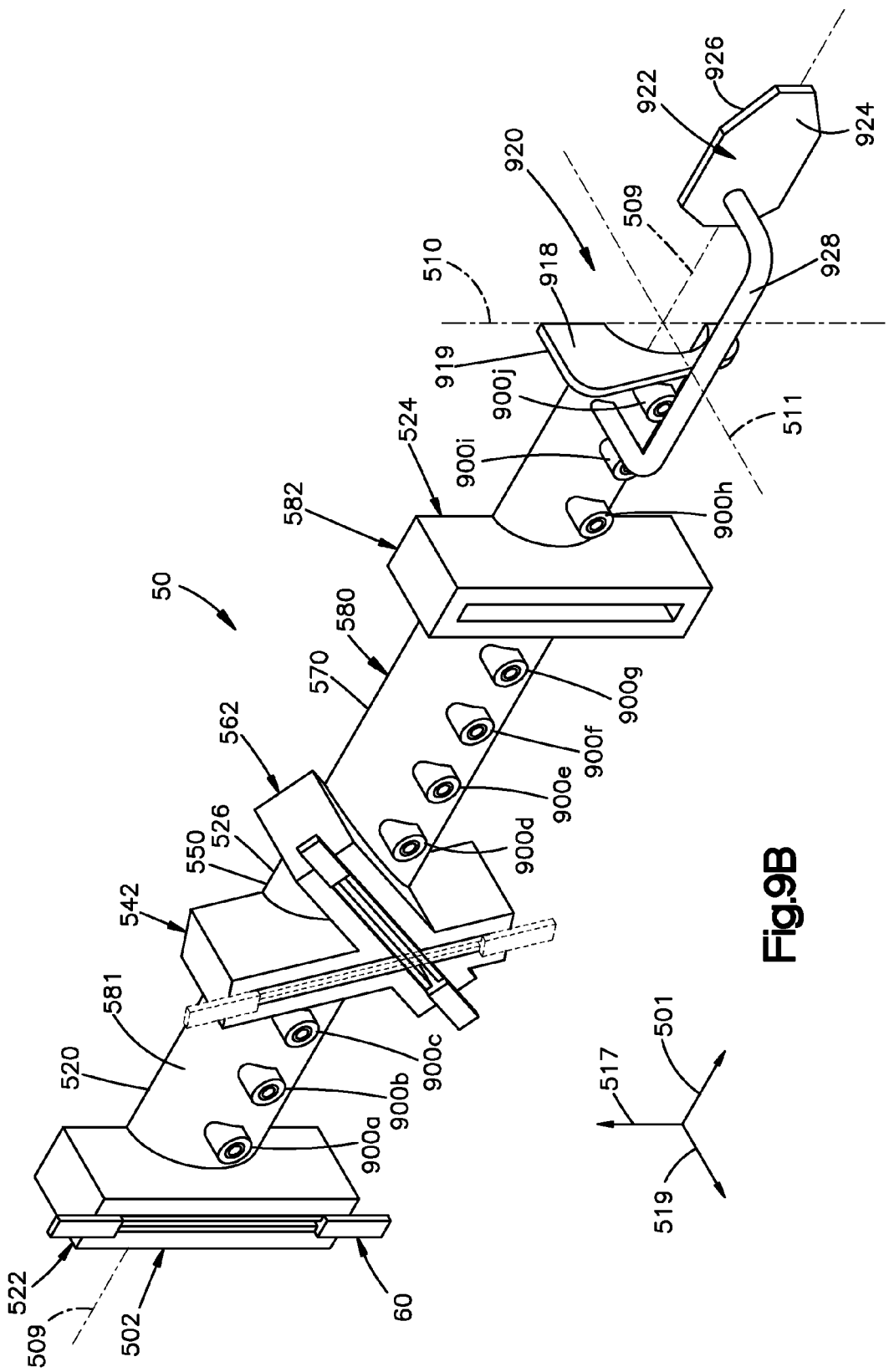
FIG. 9B is a front perspective view of a resection guide of FIG. 9A including a resection guide body, guide members and a support member.

Referring to FIGS. 9A and 9B, in accordance with an alternative embodiment, the resection guide body 580 extends between a first end 522 and a second end 916 spaced from the first end 522 along the longitudinal direction 501. The resection guide body 580 defines an upper body surface 581 and a lower body surface 577 that is opposite to and spaced from the upper body surface 581 along the transverse direction 519. The lower body surface 577 is configured to be placed against the graft source 403. The resection guide 110 defines a longitudinal central axis 509 that is aligned with and extends along the longitudinal direction 501, a lateral axis 510 that is perpendicular to the central axis 509, and a transverse axis 511 that is perpendicular to the lateral axis 510 and the central axis 509. The lateral and transverse axes 510 and 511 may considered first and second radial axes 509 and 510, for instance, when the resection guide body 580 has curved profile as illustrated in FIGS. 9A and 10A-11B. The central axis 509, lateral axis 510, and transverse axis 511 intersect at a point 806.

It should be appreciated that the resection guide axes 509, 510 and 511 correspond to and are aligned with graft source axes 459, 460, and 461. For instance, the graft source 403 can define a central axis 459 extending along a length of the graft source 403, a lateral axis 460 that is perpendicular to the central axis 459, and a transverse axis 461 that is perpendicular to the lateral axis 460 and the central axis 459. The graft source lateral axis 460 and graft source transverse axis 461 can be defined as perpendicular first and second radial axes 460 and 461.

Further, the resection guide body 580 includes a first resection guide supporting member 502, a second resection guide supporting member 542, a third resection guide supporting member 562, and a fourth resection guide supporting member 582 configured similar to the resection guide 60 described above. The resection guide body 580 also includes a plurality of connection members 520, 550, 570 each of which couple respective adjacent resection guide supporting members 502, 542, 562, and 582 together. A resection guide member, such as resection guide members 60 and/or 80, can be disposed in the opening of the resection guide support member 502, 542, 562, and 582. The resection guide body 580 can further define one or more holes 587 that are configured to receive therethrough a fastener, such as a bone screw, used to couple the guide body 580 to the graft source 403 during resection of graft portions 409 and 411 and formation of the graft bores 420. Further, the resection guide body 580 can be a monolithic metallic material or polymeric material, similar to the embodiment shown in FIG. 8, such that the resection guide support members are monolithic with the resection guide body 580 and define the resection guide members 60.

In accordance with the alternative embodiment, the resection guide body 580 defines a flange 917 disposed at the second end 916 of the resection guide body 580. The flange 917 is configured to guide a cutting tool toward the graft source 403. The resection guide body 580 illustrated in FIGS. 9A-11B include a fourth connection member 590 the couples resection guide support member 582 to the flange 917 such that the flange 917 is spaced from the resection guide support member 582 along the longitudinal direction 509. The flange 917 protrudes from the body surface 581 along the transverse direction 519 and the lateral direction 517. The flange 917 includes a first surface 918 and a second surface 919 spaced from the first surface 918. The first surface 918 defines a guide surface, which is configured to guide a cutting tool toward the graft source 403. It should be appreciated that the flange 917 can be oriented relative resection guide body 580 such that guide surface 918 can guide a resection tool 300 along a desired resection axis, such as first resection 591 (FIG. 1A). For instance, the flange 917 can be oriented on the resection guide body 580 such that the guide surface 918 is angularly offset relative to the lateral axis 510 (FIG. 9A) so as to define a flange angle π between the surface 918 and central axis 509. The flange angle π can be oblique, for instance acute or obtuse, depending on the desired graft 408 configuration. For instance, the flange 917 can be oriented on the resection guide body 580 such that the guide surface 918 is perpendicular to the central axis 509.

The resection guide 110 can also include a support member 920 extending from the resection guide body 580 and configured to support the resection guide 110 on the patient. The support member 920 includes a support plate 922 and a beam 928 connecting the plate 922 to the resection guide body 580. The plate 922 defines a tissue contact surface 926 and plate surface 924 opposite the tissue contact surface 926. The beam 928 defines a first end 928a and a terminal end 925b spaced from the first end 928a. The beam first end 925a is coupled to or integral with the connection member 590 on the resection guide body 580, while beam terminal end 925b is coupled to or integral with the plate 922. The beam 928 can arch along the transverse direction 519 over flange 917. The support member 920 can be a monolithic, for instance the beam 928 and plate 922 are monolithic. The support member 920 can be coupled to the support guide body 580 or monolithic with support guide body 580. The resection guide 110 can include one or more support members 920, for instance a first support member (not shown) and second support member (not shown) disposed at the first end 522 of the resection guide body 580. In other embodiments, the support member 920 can one include or more multiple beams 928 each having a support plates disposed on the terminal ends of the beams. Further, the support member can define one or more beams with a bulb or an enlarged portion disposed a terminal end of the beam.

The drilling guide members 900 are configured to receive and guide a tool, such as a drill bit, toward to the graft source 403 to form the graft bores 420 (FIG. 10A) in the graft source 403. Referring to FIGS. 9B-11B, the resection guide 110 includes at least one drill guide member 900 disposed along the resection guide body 580. At least one (a plurality is illustrated) drilling guide member 900 is disposed on one or more of the connection members 520, 550, 570 and 590. For instance, in the embodiment shown in FIG. 9B, the first connection member 520 includes drilling guide members 900a-900c, the third connection member can include guide members 900d-900g, and fourth connection member 590 includes drilling guide members 900h-900j. The quantity of drilling guide members 900, as well as the location and angular orientation of the drilling guide members 900 on the resection guide body 580 can vary depending on the patient anatomy, such as configuration of the desired graft 408, graft source 403, and type and/or size of the intended bone fixation plate.

Referring to FIGS. 9B-9D, the drilling guide member 900 protrudes from the upper surface 581 of the resection guide body 580 along a transverse direction 519. The resection guide body 580 defines a drilling guide body 902 that extends or protrudes from the upper surface 581 of the resection guide body 580 to a drilling guide tip 903. The drilling guide body 902 defines an outer surface 906 and an inner surface 908 spaced from the outer surface 906. The inner surface 908 defines a throughbore 907 that extends through the body 902 between the lower surface 577 of the resection body 580 and the tip 903 of the drilling guide body 902. The guide member 900 defines guide member axis 901 extending through and along the throughbore 907.

The drilling guide member 900 also supports or carries a sleeve 904. The sleeve 904 can define a sleeve body 905 extending between a distal end 904e and proximal end 904p spaced from the distal end 904e along the guide member axis 901. When the sleeve 904 is disposed in the guide body 902, the sleeve distal end 904e is positioned proximate or aligned with the resection guide lower surface 577 and the proximal end 904p is proximate to or aligned with the guide member tip 903. The sleeve body 905 further defines a throughbore 914 extending through the sleeve body 905 between the distal end 904e and the proximal end 904p. The sleeve body 905 has an outer surface 910 and inner surface 912 spaced from the outer surface 910. The sleeve 904 is positioned at least partially in the throughbore 907 of guide body 902 such that the sleeve outer surface 910 is adjacent to the guide body inner surface 908. The sleeve body inner surface 912 defines a throughbore 914. The throughbore 914 is sized to receive a tool therethrough, such as a portion of the drill bit. The guide member body 902 and the sleeve 904 can be formed of the same or dissimilar materials. The sleeve 904 can be formed of materials similar to the resection guide members 60 and 80 discussed above. When the sleeve 904 is formed of a cut-resistant material, for instance a metallic material, drilling accuracy is improved, and tissue contamination during resection/reconstruction procedure from debris can be minimized.

Figure 10A:
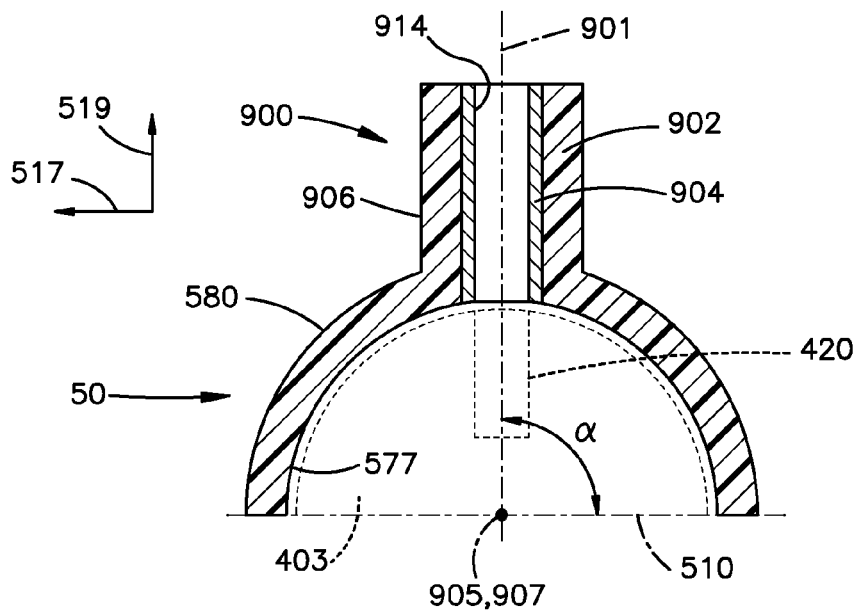
FIGS. 10A through 10C are cross-sectional views of the resection guide taken along lines 10A-10A, illustrating various orientations of the drilling guide member on the resection guide body, according to an embodiment of the disclosure.

Referring to FIGS. 10A-11B, the drilling guide members 900 can be configured, for instance oriented, on the resection guide 110 depending on the patient anatomy contemplated bone fixation plates that will used to couple the graft 408 to the tissue body 400. For instance, the drilling guide member 902 can oriented and/or positioned on the resection guide 110 such that the drill bit can form a graft bore 420 that is the appropriate size, shape and orientation of the graft source 408 so as to receive the bone anchors therein as discussed above. Each graft bore 420 can define a graft bore axis 419 that extends along the length of the bore 420. Referring to FIG. 10A-10C, the drilling guide member 900 can be configured so that the drilling guide axis 901 defines an angle $\alpha$ with respect to the lateral axis 510. The angle $\alpha$ can be about 90 degrees as shown in FIG. 10A or oblique. For instance angle $\alpha$ can be acute as shown in FIGS. 10B and 10C or obtuse (not shown).

As shown in FIG. 10A, the drill guide member 900 is configured such that the drilling guide axis 901 intersects and is perpendicular to the lateral axis 510 and the central axis at a point 907, and is parallel or aligned with transverse axis 511. The drilling guide member 900 shown in FIG. 10A can be used to form a graft bore 420a in the graft source 403 that is oriented with drilling guide axis 901 as illustrated, for instance parallel or aligned with transverse axis 511 of the resection guide body 580. The dimensions of the graft bore, such as the width and depth can be control with the drill bit. In the embodiment shown in FIG. 10C, the drilling guide axis 901 intersects the lateral axis 510, the transverse axis 511, and the central axis at a point 907, similar to the embodiment shown in FIG. 10A. The drilling guide member 900 shown in FIG. 10A can be used to form a graft bore 420c in the graft source 403 that is oriented with drilling guide axis 901 as illustrated. For instance, the bore 420c is oriented such that the bore axis 419 is acute with respect to graft source transverse axis 461.

Figure 10B:
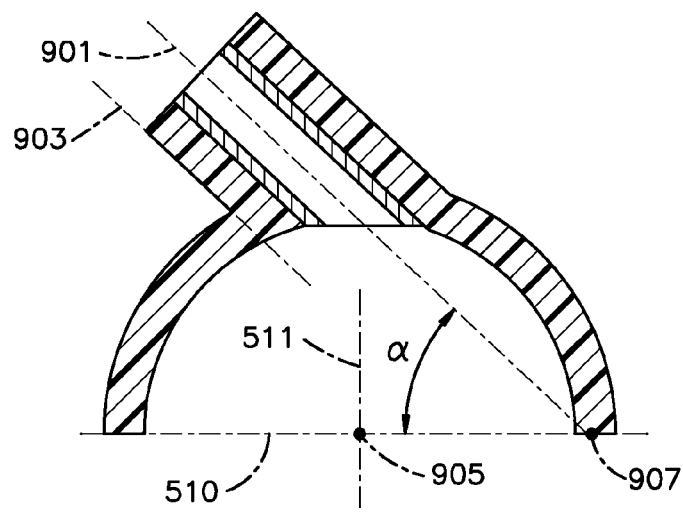
Figure 10C:
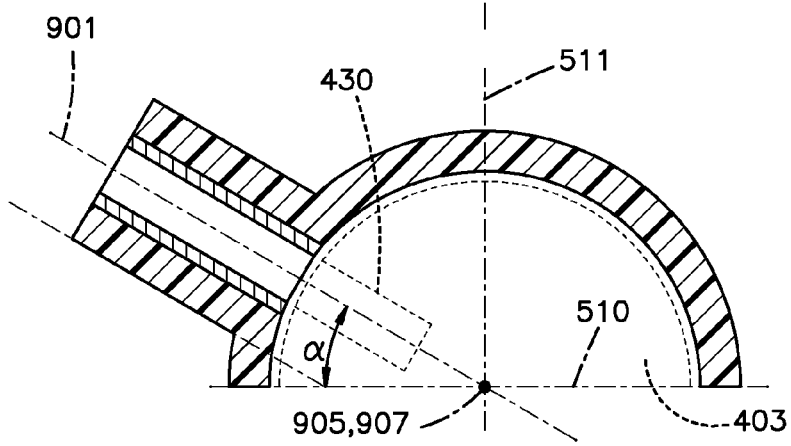

The drilling guide member 900 can be positioned at any location along the upper surface 581 of the resection guide body 580 such that the guide member body 905 is perpendicular to the upper surface 581. Referring to FIG. 10B, the drilling guide member 900 is oriented such the that guide member body 905 is inclined with respect to the upper surface 581 such that the drilling guide axis 901 is acute with the respect the lateral axis 510, and intersects the lateral axis 510 at a point 909 that is offset from the central axis 509 and the transverse axis 511. In FIG. 10B, drilling guide member 900 is configured such that the drilling guide axis 901 is acute relative to the lateral axis 510 and intersects the lateral axis 510 at a point 909 that is offset from the central axis 509 and lateral axis 511. The drilling guide member 900 shown in FIG. 10B can be used to form a graft bore 420b in the graft source 403 that is oriented with drilling guide axis 901. For instance the graft bore 420b is oriented such that bore axis 419 is at an acute angle with respect to the graft source lateral axis 461, and is aligned with the surface of the graft source 403.

Figure 11A:
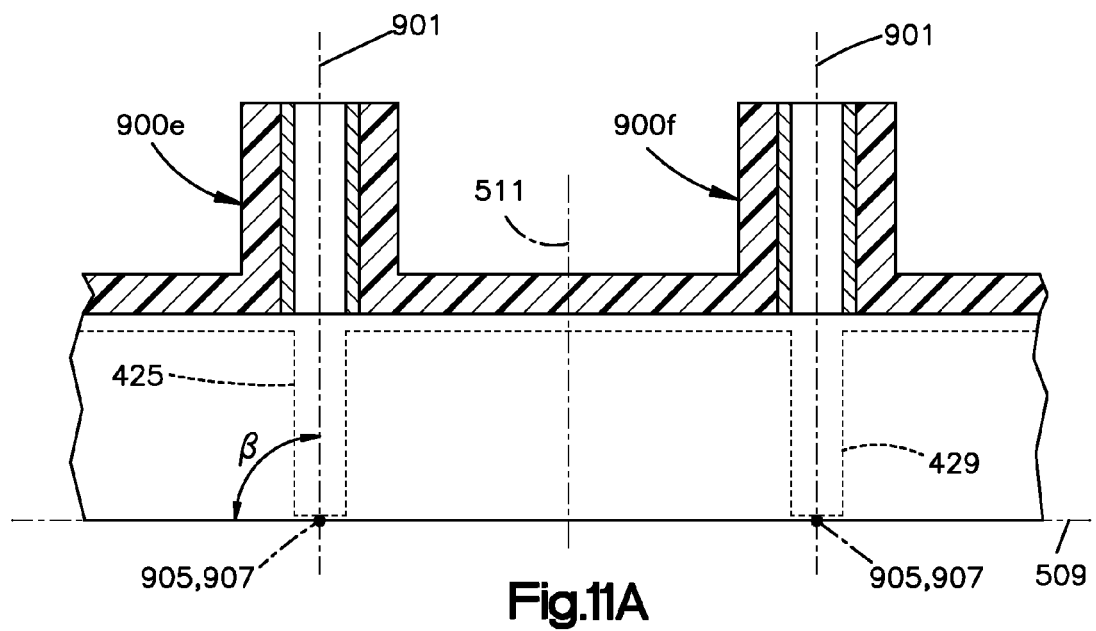
FIGS. 11A through 11B are cross-sectional views of the resection guide taken along lines 11-11, illustrating the orientations of the drilling guide member on the resection guide body, according to an embodiment of the disclosure
Figure 11B:
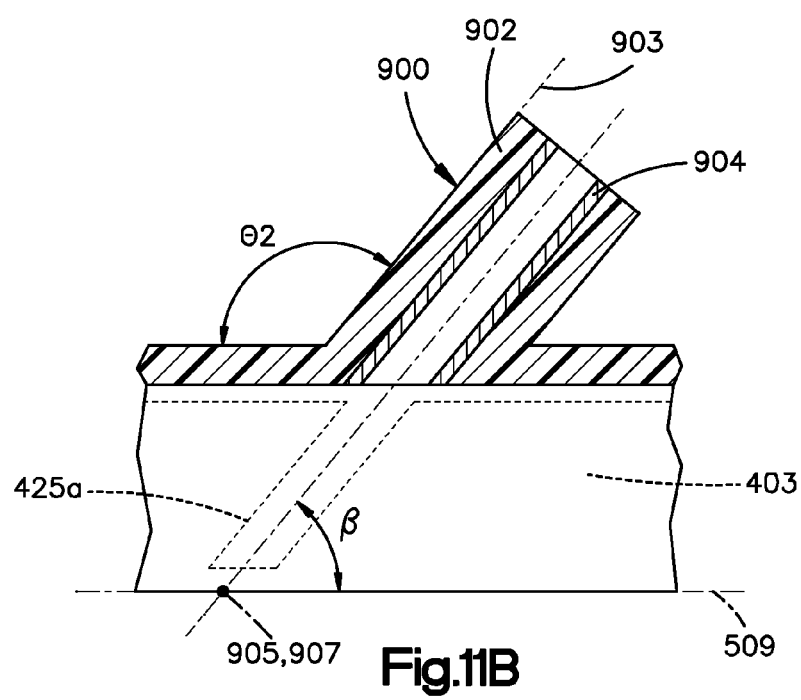

Turning to FIGS. 11A and 11B, the drilling guide member 900 can be oriented toward either opposing end 522 or 525 of the resection guide body 580 such that the drilling guide body 905 defines an angle $\theta2$ with respect to the upper surface 581. Angle $\theta2$ can be equal to 90 degrees as shown in FIG. 11A or oblique, for instance angle $\theta2$ can be obtuse as shown in FIG. 11B, or acute (not shown). The drilling guide axis 901 can define an angle $\beta$ with respect to the central axis 509. Angle $\beta$ can be equal to about 90 degrees as shown in FIG. 11A, acute as shown in FIG. 11B, or obtuse (not shown). The drilling guide members 900e and 900f shown in FIG. 11A guides a tool into a graft source 403 to form graft bores 420e and 420f that are aligned with the lateral axis 511 of the resection guide body 580, and thus the graft source lateral axis 461. The drilling guide member 900 shown in FIG. 11B guides a tool into a graft source 403 to form graft bores 422 that are oriented toward either opposing end 522 or 525 of the resection guide body. Such a configuration forms a graft bore 422 that is oriented such that bore axis 419 is at an acute angle with respect to the central axis of the graft source 403.

It should be appreciated that the drilling guide member 900 can be oriented in any direction relative to the resection guide body 580 by varying one or more of the angle $\alpha$, angle $\beta$, angle $\theta1$, and angle $\theta2$ angles. For instance, the drilling guide member 900 can disposed on the resection guide body 580 such that at least one of the of angle $\alpha$ and angle $\beta$ is acute, a right angle, or obtuse. For instance, angle $\alpha$ and angle $\beta$ can both be acute, right angles, or obtuse angles. Alternatively, angle $\alpha$ can be acute and angle $\beta$ can be a right angle or obtuse. The drilling guide member 900 can disposed on the resection guide body 580 such that one or both angle $\theta1$ and angle $\theta2$ is acute, a right angle, or obtuse. The drilling guide members 900 can configured during the design and development of the resection guide 110 using the scanning and three-dimensional modeling technologies discussed above.

Figure 12A:
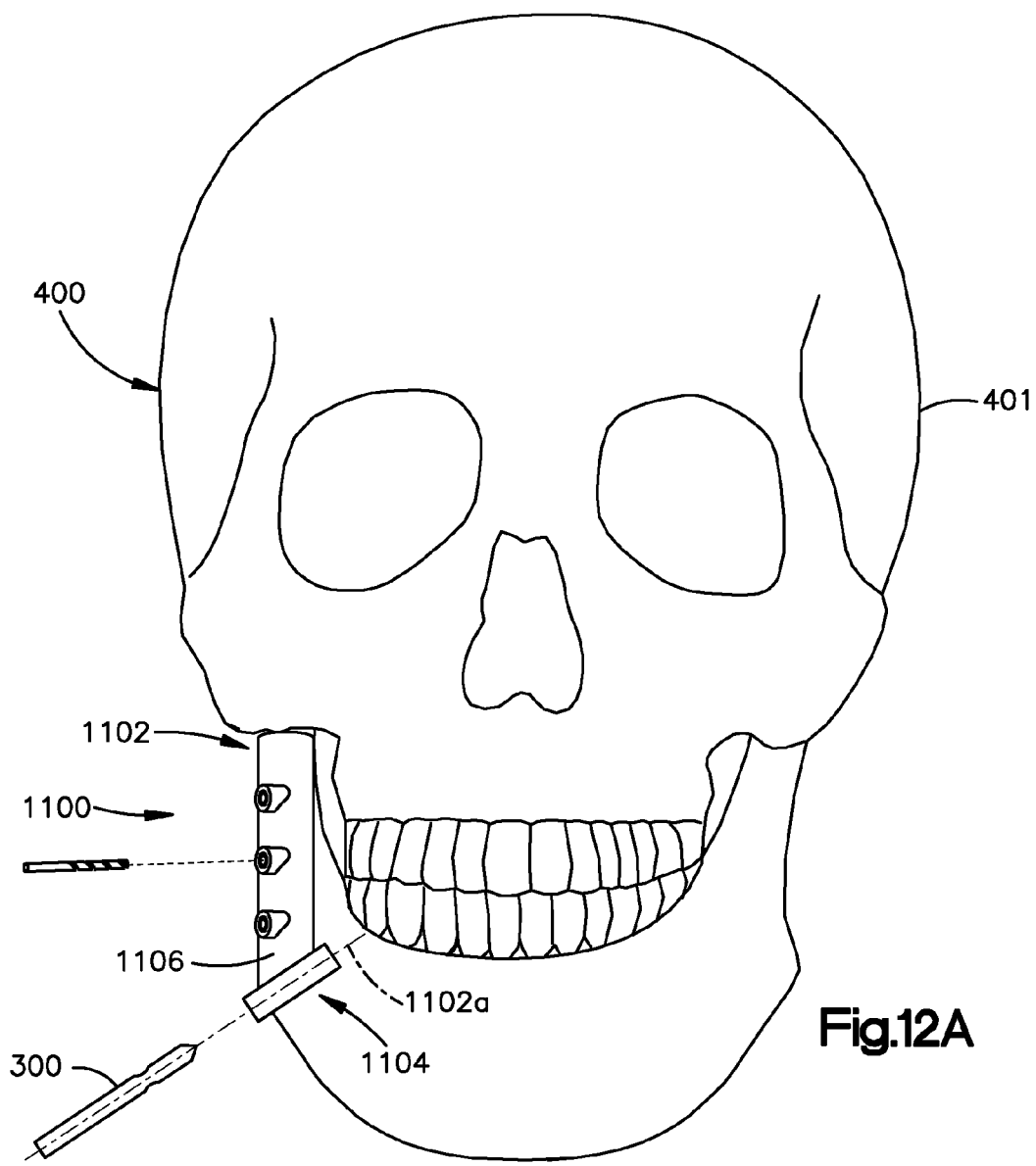
FIG. 12A is a perspective view of a resection guide coupled to a skull according to an embodiment of the present disclosure.
Figure 12B:
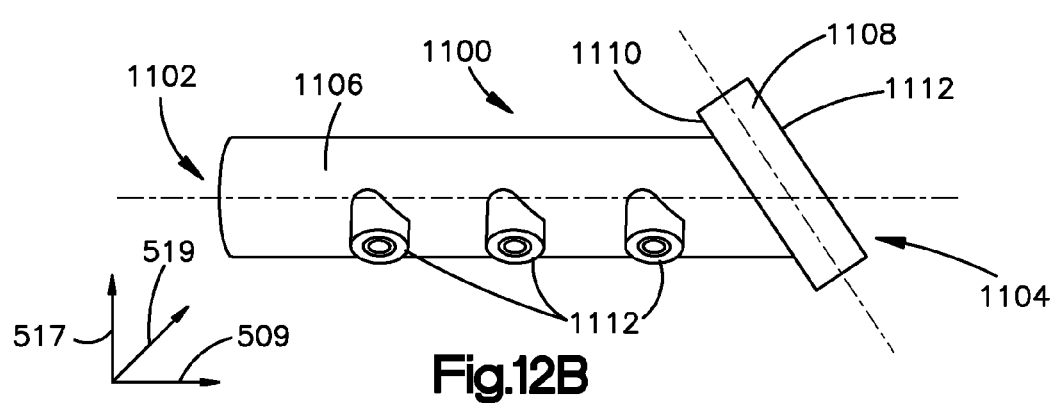
FIG. 12B illustrates the resection guide shown in FIG. 12A.

Referring to FIGS. 12A and 12B, in accordance with an alternative embodiment of resection guide 1100 configured to resect tissue from the tissue body 400, the resection guide 1100 can be configured to be coupled to the tissue body 400 at the desired resection site. For example, the resection guide 1100 can be configured to be coupled to the tissue body 400 so as to define a resection axis 102a. The resection guide 1110 The resection guide 110 can be a patient specific resection guide, designed and manufactured as described above in other embodiments of the present disclosure, for example similar to the resection guide 200 described above. In accordance with the alternative embodiment, the resection guide 1100 can include one or more resection guide members, and one or more drilling guide members 1900 that are configured, or can be configured, similar to the drilling guide members 900 shown in FIGS. 9A-11B. The drilling guide members 1900 guide a tool toward the tissue body 400 such the tool, such as drill bit can form tissue body bores 430 in the tissue body 400 at specific locations that can align the holes in a bone fixation plate used to couple the graft 408 to the tissue body 400.

The resection guide 1100 can define a resection guide body 1106 extending between a first end 1102 and a second end 1104 spaced from the first end along a longitudinal direction 501. The resection guide 1100 defines a longitudinal central axis 1101 that is aligned with and extends along the longitudinal direction 501, a lateral axis 1114 that is perpendicular to the central axis 1101, and a transverse axis 1116 that is perpendicular to the lateral axis 1114 and the central axis 1101. The lateral and transverse axes 1114 and 1116 may considered first and second radial axes 1114 and 1116, for instance, when the resection guide body 1106 has a curved profile.

The resection guide body 1106 defines a flange 1108 disposed at the second end 1104 of the resection guide body 1106. The flange 1108 is configured to guide a cutting tool toward the tissue body 400. The flange 1108 protrudes from the resection guide body 1106 along the transverse direction 519 and the lateral direction 517. The flange 1108 includes a first surface 1110 and a second or guide surface 1112 spaced from the first surface 1110 along the longitudinal direction 501. The guide surface 112 is configured to guide a cutting tool toward the graft tissue body 400. It should be appreciated that the flange 1108 can be oriented relative resection guide body 1106 such that guide surface 1112 can guide a resection tool 300 along a desired resection axis, such as first resection 102a. The flange 1108 can include coating and/or a plate positioned adjacent the guide surface 1112. The plate (not shown) can size an dimensioned to conform to the surface area of the guide surface 1112. The plate can be formed of a hardened polymeric material as described above, or a metallic material or alloy. The plate is configured to guide the resection tool, improve cutting accuracy, and minimize debris from being removed from the resection guide body 1106. The coating can be any material, such as a composition, polymer or polymeric blend applied to the guide surface 1112 so as to create a cut-resistant surface. The resection guide 1100 can be formed with any of the materials and processes described above.

It should be noted that the illustrations and discussions of the embodiments shown in the figures are for exemplary purposes only, and should not be construed limiting the disclosure. One skilled in the art will appreciate that the present disclosure contemplates various embodiments. It should be further appreciated that the features and structures described and illustrated in accordance one embodiment can apply to all embodiments as described herein, unless otherwise indicated. Additionally, it should be understood that the concepts described above with the above-described embodiments may be employed alone or in combination with any of the other embodiments described above.

What is claimed:

1. A resection guide configured to guide a resection tool toward a graft source, the resection guide comprising:
   a resection guide body defining:
      an external, outer body surface;
      an inner body surface opposite the outer body surface and elongate along a longitudinal direction, the inner body surface having a first terminal edge and a second terminal edge offset from the first terminal edge by a first dimension along a select direction that is perpendicular to the longitudinal direction, and the inner body surface being concave from the first terminal edge to the second terminal edge; and
      first and second resection guide openings that extend from the inner body surface through the outer body surface, wherein the first and second resection guide openings define respective first and second graft resection axes that are configured to receive a portion of the resection tool and guide the resection tool along the respective first and second resection guide openings so as to resect a graft portion from the graft source, the resection guide body defining, for each one of the first and second resection guide openings, first and second inner surfaces that at least partially define the one of the first and second resection guide openings, wherein the second inner surface is spaced from the first inner surface along a respective one of the first and second graft resection axes, and the second inner surface is offset from the first inner surface by a minimum dimension with respect to the select direction, the minimum dimension being greater than the first dimension.

2. The resection guide according to claim 1, wherein the resection guide body defines, for each of the first and second resection guide openings, third and fourth opposed inner surfaces that at least partially define the respective one of the first and second resection guide openings and are configured to contact the resection tool as the resection tool is guided along the respective first and second graft resection axes.

3. The resection guide according to claim 1, wherein the first and second resection guide openings are devoid of inserts that are discrete with the resection guide body.

4. The resection guide according to claim 1, wherein the resection guide body is laser-sintered.

5. The resection guide according to claim 1, wherein the first and second graft resection axes are angularly offset with respect to each other.

6. The resection guide according to claim 1, wherein the resection guide body is made from a metallic material that has a Brinell hardness ranging between about 10 HB and about 200 HB.

7. The resection guide according to claim 1, wherein the resection guide body is made from a metallic material that has a Brinell hardness of about 120 HB.

8. The resection guide of claim 1, wherein the first resection guide opening is spaced from the second resection guide opening.

9. The resection guide of claim 8, further comprising a third resection guide opening that extends from the inner body surface through the outer body surface, the third resection guide opening intersecting one of the first and second resection guide openings.

10. The resection guide of claim 1, wherein the first resection guide opening intersects the second resection guide opening.

11. The resection guide of claim 2, wherein the resection guide body is elongate along a central axis that extends in the longitudinal direction, and the first and second inner surfaces are spaced further from the central axis along the select direction than the first and second terminal edges.

12. The resection guide of claim 1, wherein the resection guide body is elongate along a central axis that extends in the longitudinal direction, and the first and second inner surfaces are spaced further from the central axis along the select direction than the first and second terminal edges.

13. The resection guide of claim 1, wherein the resection guide body defines, for each of the first and second resection guide openings, third and fourth inner surfaces that extend between the first and second inner surfaces so as to at least partially define the respective one of the first and second resection guide openings, wherein the first inner surface faces the second inner surface and the third inner surface faces the fourth inner surface.

14. The resection guide of claim 1, wherein the resection guide body comprises:
   first and second support members defining the first and second resection guide openings, respectively; and
   a connecting member connecting the first support member to the second support member, wherein each of the first and second support members have a length in a direction that is greater than a length of the connecting member in the direction.

15. The resection guide of claim 1, wherein, for each of the first and second resection guide openings, an inner surface of the resection guide body defines a closed shape around the respective one of the first and second resection guide openings, the closed shape lying in a single plane.

16. The resection guide of claim 1, wherein the resection guide body is elongate along a longitudinal direction, and at least one of the first and second resection guide openings is elongate in a direction perpendicular to the longitudinal direction.

17. A resection guide configured to guide a resection tool toward a graft source, the resection guide comprising:
   a resection guide body defining:
      an external, outer body surface;
      an inner body surface opposite the outer body surface and elongate along a longitudinal direction, the inner body surface having a first terminal edge and a second terminal edge spaced from the first terminal edge along a select direction that is perpendicular to the longitudinal direction, and the inner body surface being concave from the first terminal edge to the second terminal edge; and first and second resection guide openings that extend from the inner body surface through the outer body surface, and that intersect one another and at least one of the first and second terminal edges, wherein the first and second resection guide openings define respective first and second graft resection axes that are configured to receive a portion of the resection tool and guide the resection tool along the respective first and second resection guide openings so as to resect a graft portion from the graft source.

18. The resection guide according to claim 17, wherein the resection guide body defines, for each of the first and second resection guide openings, first and second opposed inner surfaces that at least partially define the respective one of the first and second resection guide openings and are configured to contact the resection tool as the resection tool is guided along the respective first and second graft resection axes.

19. The resection guide of claim 18, wherein the resection guide body defines, for each of the first and second resection guide openings, third and fourth opposed inner surfaces that extend between the first and second opposed inner surfaces and at least partially define the respective one of the first and second resection guide openings, wherein the first and second terminal edges of the inner body surface are spaced between the third and fourth inner surfaces.

20. The resection guide of claim 17, wherein the resection guide body defines, for each of the first and second resection guide openings, a first inner surface and a second inner surface spaced from the first inner surface so as to at least partially define the respective one of the first and second resection guide openings, wherein the first and second terminal edges of the inner body surface are spaced between the first and second inner surfaces.

21. The resection guide of claim 17, wherein the resection guide body defines, for each of the first and second resection guide openings, opposed first and second inner surfaces and opposed third and fourth inner surfaces, the first to fourth inner surfaces at least partially defining the respective one of the first and second resection guide openings, wherein the first inner surface faces the second inner surface and the third inner surface faces the fourth inner surface.

22. The resection guide of claim 17, wherein the resection guide body comprises:

first and second support members defining the first and second resection guide openings, respectively; and a connecting member connecting the first support member to the second support member, wherein each of the first and second support members have a length in the direction that is greater than a length of the connecting member in the direction.

23. The resection guide of claim 17, wherein, for each of the first and second resection guide openings, an inner surface of the resection guide body defines a closed shape around the respective one of the first and second resection guide openings, the closed shape lying in a single plane.

24. The resection guide of claim 17, wherein the resection guide body is elongate along a longitudinal direction, and at least one of the first and second resection guide openings is elongate in a direction perpendicular to the longitudinal direction.

25. The resection guide of claim 8, wherein the resection guide body defines a second minimum dimension from the first resection guide opening to the second resection guide opening along the longitudinal direction that is greater than the first dimension from the first terminal edge to the second terminal edge along the select direction.

26. The resection guide of claim 17, wherein the resection guide body defines, for each resection guide opening of the first and second resection guide openings, a first inner surface and a second inner surface spaced from the first inner surface along a respective one of the first and second graft resection axes such that the resection guide opening is elongate from the first inner surface to the second inner surface, and wherein the first inner surface of the first resection guide opening is spaced from the first inner surface of the second resection guide opening with respect to the longitudinal direction.

* * * * *